(12) United States Patent
Zhao et al.

(10) Patent No.: US 11,981,741 B2
(45) Date of Patent: May 14, 2024

(54) HUMANIZED ANTI-CD45 ANTIBODIES

(71) Applicant: ACTINIUM PHARMACEUTICALS, INC., New York, NY (US)

(72) Inventors: Lequn Zhao, San Carlos, CA (US); Helen Kotanides, New York, NY (US)

(73) Assignee: Actinium Pharmaceuticals, Inc., New York, NY (US)

( * ) Notice: Subject to any disclaimer, the term of this patent is extended or adjusted under 35 U.S.C. 154(b) by 0 days.

(21) Appl. No.: 18/464,847

(22) Filed: Sep. 11, 2023

(65) Prior Publication Data

US 2024/0010744 A1  Jan. 11, 2024

Related U.S. Application Data

(63) Continuation-in-part of application No. PCT/US2023/064941, filed on Mar. 24, 2023.

(60) Provisional application No. 63/407,979, filed on Sep. 19, 2022, provisional application No. 63/405,237, filed on Sep. 9, 2022, provisional application No. 63/323,257, filed on Mar. 24, 2022.

(51) Int. Cl.
   *C07K 16/28* (2006.01)
   *A61K 51/10* (2006.01)

(52) U.S. Cl.
   CPC ........ *C07K 16/289* (2013.01); *A61K 51/1027* (2013.01); *C07K 2317/565* (2013.01)

(58) Field of Classification Search
   CPC ............ C07K 16/289; C07K 2317/565; C07K 2317/24; C07K 2317/92; A61K 51/1027; A61K 51/1069; A61K 51/1096
   See application file for complete search history.

(56) References Cited

U.S. PATENT DOCUMENTS

| | | | |
|---|---|---|---|
| 9,603,954 B2 | 3/2017 | Simon et al. | |
| 10,420,851 B2 * | 9/2019 | Dave | C07K 16/3061 |
| 10,736,975 B2 | 8/2020 | Dave et al. | |
| 11,406,724 B2 | 8/2022 | Dave et al. | |
| 2013/0333061 A1 | 12/2013 | Wu et al. | |
| 2015/0079093 A1 | 3/2015 | Stuhler | |
| 2015/0274827 A1 | 10/2015 | Pfizenmaier et al. | |
| 2017/0326259 A1 | 11/2017 | Dave et al. | |
| 2018/0237521 A1 | 8/2018 | Finney et al. | |
| 2020/0306301 A1 | 10/2020 | Andresen et al. | |
| 2020/0330514 A1 * | 10/2020 | Andresen | A61K 39/464463 |
| 2020/0338219 A1 | 10/2020 | Ludwig | |
| 2022/0175951 A1 | 6/2022 | Boitano et al. | |
| 2022/0378955 A1 | 12/2022 | Ludwig et al. | |

FOREIGN PATENT DOCUMENTS

| | | |
|---|---|---|
| WO | 2017155937 A1 | 9/2017 |
| WO | 2022040577 A1 | 2/2022 |

OTHER PUBLICATIONS

International Search Report and Written Opinion dated Sep. 19, 2023 for corresponding International Application No. PCT/US2023/064941.
Arslan et al., Effect of non-repetitive linker on in vitro and in vivo properties of an anti-VEGF scFv, Scientific Reports, (2022) 12:5449, 8 pgs.
Lin et al., A Genetically Engineered Anti-CD45 Single-Chain Antibody-Streptavidin Fusion Protein for Pretargeted Radioimmunotherapy of Hematologic Malignancies, Cancer Res 2006; 66: (7). Apr. 1, 2006, 3884-3892.
Shen et al., Engineering Peptide Linkers for scFv Immunosensors, Anal Chem. Mar. 15, 2008; 80(6): 1910-1917.

* cited by examiner

*Primary Examiner* — Hong Sang
*Assistant Examiner* — Carol Ann Chase
(74) *Attorney, Agent, or Firm* — Dentons Cohen & Grigsby P.C.

(57) ABSTRACT

Provided are humanized anti-human CD45 antibodies and pharmaceutical compositions including the antibodies.

11 Claims, 14 Drawing Sheets

Specification includes a Sequence Listing.

mAb chain ID: m CD45-HC parental

(hHeavy-m CD45-HC parental; Human IgG1 (G1m17)

Signal peptide: MDPKGSLSWRILLFLSLAFELSYG (SEQ ID NO:1)

Heavy chain variable region:

EVKLLESGGGLVQPGGSLKLSCAASGFDFSRYWMSWVRQAPGKGLEWIGEINPTSSTIN
FTPSLKDKVFISRDNAKNTLYLQMSKVRSEDTALYYCARGNYYRYGDAMDYWGQGTS
VTVSS (SEQ ID NO:2)

CDR$_{H1}$: GFDFSRYWMS (SEQ ID NO:53), CDR$_{H2}$: EINPTSSTINFTPSLKD (SEQ ID NO:54),
CDR$_{H3}$: GNYYRYGDAMDY (SEQ ID NO:55)

1$^{st}$ Residue: A    Heavy chain constant region with 1$^{st}$ Residue: SEQ ID NO:4

Heavy chain constant region:

STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO:3)

Full length heavy chain including signal peptide:

MDPKGSLSWRILLFLSLAFELSYGEVKLLESGGGLVQPGGSLKLSCAASGFDFSRYWMS
WVRQAPGKGLEWIGEINPTSSTINFTPSLKDKVFISRDNAKNTLYLQMSKVRSEDTALYY
CARGNYYRYGDAMDYWGQGTSVTVSSASTKGPSVFPLAPSSKSTSGGTAALGCLVKD
YFPEPVTVSWNSGALTSGVHTFPAVLQSSGLYSLSSVVTVPSSSLGTQTYICNVNHKPSN
TKVDKKVEPKSCDKTHTCPPCPAPELLGGPSVFLFPPKPKDTLMISRTPEVTCVVVDVSH
EDPEVKFNWYVDGVEVHNAKTKPREEQYNSTYRVVSVLTVLHQDWLNGKEYKCKVS
NKALPAPIEKTISKAKGQPREPQVYTLPPSREEMTKNQVSLTCLVKGFYPSDIAVEWESN
GQPENNYKTTPPVLDSDGSFFLYSKLTVDKSRWQQGNVFSCSVMHEALHNHYTQKSLS
LSPG (SEQ ID NO:5)

Full length heavy chain without signal peptide: (SEQ ID NO:6)

FIG. 1 mAb chain ID: hu CD45.HC1

(hHeavy-hu CD45.HC1; Human IgG1 (G1m17))

Signal peptide: MDPKGSLSWRILLFLSLAFELSYG (SEQ ID NO:1)

Heavy chain variable region:

EVQLVESGGGLVQPGGSLRLSCAASGFDFSRYWMSWVRQAPGKGLEWVSEINPTSSTIN
FADSVKGRFFISRDNAKNSLYLQMNSLRAEDTAVYYCARGNYYRYGDAMDYWGQGT
MVTVSS (SEQ ID NO:7)

CDR$_{H1}$: GFDFSRYWMS (SEQ ID NO:53), CDR$_{H2}$: EINPTSSTINFADSVKG (SEQ ID NO:56), CDR$_{H3}$: GNYYRYGDAMDY (SEQ ID NO:55)

1$^{st}$ Residue: A    Heavy chain constant region with 1$^{st}$ Residue: SEQ ID NO:9

Heavy chain constant region:

STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO:8)

Full length heavy chain including signal peptide:

MDPKGSLSWRILLFLSLAFELSYGEVQLVESGGGLVQPGGSLRLSCAASGFDFSRYWMS
WVRQAPGKGLEWVSEINPTSSTINFADSVKGRFFISRDNAKNSLYLQMNSLRAEDTAVY
YCARGNYYRYGDAMDYWGQGTMVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSL
SLSPG (SEQ ID NO:10)

Full length heavy chain without signal peptide: SEQ ID NO:11

FIG. 2 mAb chain ID: hu CD45.HC2

(hHeavy-hu CD45.HC2; Human IgG1 (G1m17))

Signal peptide: MDPKGSLSWRILLFLSLAFELSYG (SEQ ID NO:1)

Heavy chain variable region:

EVQLLESGGGLVQPGGSLRLSCAASGFDFSRYWMSWVRQAPGKGLEWVSEINPTSSTIN
YADSVKGRFTISRDNSKNTLYLQMNSLRAEDTAVYYCARGNYYRYGDAMDYWGQGT
MVTVSS (SEQ ID NO:12)

CDR$_{H1}$: GFDFSRYWMS (SEQ ID NO:53), CDR$_{H2}$: EINPTSSTINYADSVKG (SEQ ID NO:57), CDR$_{H3}$: GNYYRYGDAMDY (SEQ ID NO:55)

1$^{st}$ Residue: A    Heavy chain constant region with 1$^{ST}$ Residue: (SEQ ID NO:14)

Heavy chain constant region:

STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO:13)

Full length heavy chain including signal peptide:

MDPKGSLSWRILLFLSLAFELSYGEVQLLESGGGLVQPGGSLRLSCAASGFDFSRYWMS
WVRQAPGKGLEWVSEINPTSSTINYADSVKGRFTISRDNSKNTLYLQMNSLRAEDTAVY
YCARGNYYRYGDAMDYWGQGTMVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSL
SLSPG (SEQ ID NO:15)

Full length heavy chain without signal peptide: SEQ ID NO:16

FIG. 3 mAb chain ID: hu CD45.HC3

(hHeavy-hu CD45.HC3; Human IgG1 (G1m17))

Signal peptide: MDPKGSLSWRILLFLSLAFELSYG (SEQ ID NO:1)

Heavy chain variable region:

EVQLVESGGGLVQPGGSLRLSCAASGFDFSRYWMSWVRQAPGKGLEWVAEINPTSSTI
NFVDSVKGRFTISRDNAKNSLYLQMNSLRAEDTAVYYCARGNYYRYGDAMDYWGQG
TMVTVSS (SEQ ID NO:17)

CDR$_{H1}$: GFDFSRYWMS (SEQ ID NO:53), CDR$_{H2}$: EINPTSSTINFVDSVKG (SEQ ID NO:58), CDR$_{H3}$: GNYYRYGDAMDY (SEQ ID NO:55)

1$^{st}$ Residue: A    Heavy chain constant region with 1$^{st}$ Residue: SEQ ID NO:19

Heavy chain constant region:

STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO:18)

Full length heavy chain including signal peptide:

MDPKGSLSWRILLFLSLAFELSYGEVQLVESGGGLVQPGGSLRLSCAASGFDFSRYWMS
WVRQAPGKGLEWVAEINPTSSTINFVDSVKGRFTISRDNAKNSLYLQMNSLRAEDTAVY
YCARGNYYRYGDAMDYWGQGTMVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSL
SLSPG (SEQ ID NO:20)

Full length heavy chain without signal peptide: SEQ ID NO:21

FIG. 4 mAb chain ID: hu CD45.HC4

(hHeavy-hu CD45.HC4; Human IgG1 (G1m17))

Signal peptide: MDPKGSLSWRILLFLSLAFELSYG (SEQ ID NO:1)

Heavy chain variable region:

EVQLVESGGGLVKPGGSLRLSCAASGFDFSRYWMSWVRQAPGKGLEWVSEINPTSSTIN
YADSVKGRFTISRDNAKNSLYLQMNSLRAEDTAVYYCARGNYYRYGDAMDYWGQGT
MVTVSS (SEQ ID NO:22)

CDR$_{H1}$: GFDFSRYWMS (SEQ ID NO:53), CDR$_{H2}$: EINPTSSTINYADSVKG (SEQ ID NO:57), CDR$_{H3}$: GNYYRYGDAMDY (SEQ ID NO:55)

1$^{st}$ Residue: A    Heavy chain constant region with 1$^{st}$ Residue: SEQ ID NO:24

Heavy chain constant region:

STKGPSVFPLAPSSKSTSGGTAALGCLVKDYFPEPVTVSWNSGALTSGVHTFPAVLQSSG
LYSLSSVVTVPSSSLGTQTYICNVNHKPSNTKVDKKVEPKSCDKTHTCPPCPAPELLGGP
SVFLFPPKPKDTLMISRTPEVTCVVVDVSHEDPEVKFNWYVDGVEVHNAKTKPREEQY
NSTYRVVSVLTVLHQDWLNGKEYKCKVSNKALPAPIEKTISKAKGQPREPQVYTLPPSR
EEMTKNQVSLTCLVKGFYPSDIAVEWESNGQPENNYKTTPPVLDSDGSFFLYSKLTVDK
SRWQQGNVFSCSVMHEALHNHYTQKSLSLSPG (SEQ ID NO:23)

Full length heavy chain including signal peptide:

MDPKGSLSWRILLFLSLAFELSYGEVQLVESGGGLVKPGGSLRLSCAASGFDFSRYWMS
WVRQAPGKGLEWVSEINPTSSTINYADSVKGRFTISRDNAKNSLYLQMNSLRAEDTAVY
YCARGNYYRYGDAMDYWGQGTMVTVSSASTKGPSVFPLAPSSKSTSGGTAALGCLVK
DYFPEPVTVSWNSGALTSGVHTFPAVLQSSGLYSLSSVVTVPSSSLGTQTYICNVNHKPS
NTKVDKKVEPKSCDKTHTCPPCPAPELLGGPSVFLFPPKPKDTLMISRTPEVTCVVVDVS
HEDPEVKFNWYVDGVEVHNAKTKPREEQYNSTYRVVSVLTVLHQDWLNGKEYKCKV
SNKALPAPIEKTISKAKGQPREPQVYTLPPSREEMTKNQVSLTCLVKGFYPSDIAVEWES
NGQPENNYKTTPPVLDSDGSFFLYSKLTVDKSRWQQGNVFSCSVMHEALHNHYTQKSL
SLSPG (SEQ ID NO:25)

Full length heavy chain without signal peptide: SEQ ID NO:26

FIG. 5 mAb chain ID: m CD45-LC parental (hKappa-m CD45-LC parental; Human Kappa)

Signal peptide:

METDTLLLWVLLLWVPGSTG (SEQ ID NO:27)

Light chain variable region:

DIALTQSPASLAVSLGQRATISC<u>RASKSVSTSGYSYLH</u>WYQQKPGQPPKLLIY<u>LASNLES</u>
GVPARFSGSGSGTDFTLNIHPVEEEDAATYYC<u>QHSRELPFT</u>FGSGTKLEIK
(SEQ ID NO:28)

$CDR_{L1}$: RASKSVSTSGYSYLH (SEQ ID NO:59)

$CDR_{L2}$: LASNLES (SEQ ID NO:60)

$CDR_{L3}$: QHSRELPFT (SEQ ID NO:61)

$1^{st}$ Residue: R    Light chain constant region with $1^{st}$ Residue: SEQ ID NO:30

Light chain constant region:

TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO:29)

Full length light chain including signal peptide:

METDTLLLWVLLLWVPGSTGDIALTQSPASLAVSLGQRATISCRASKSVSTSGYSYLHW
YQQKPGQPPKLLIYLASNLESGVPARFSGSGSGTDFTLNIHPVEEEDAATYYCQHSRELP
FTFGSGTKLEIKRTVAAPSVFIFPPSDEQLKSGTASVVCLLNNFYPREAKVQWKVDNALQ
SGNSQESVTEQDSKDSTYSLSSTLTLSKADYEKHKVYACEVTHQGLSSPVTKSFNRGEC
(SEQ ID NO:31)

Full length light chain without signal peptide: SEQ ID NO:32

FIG. 6 mAb chain ID: hu CD45.LC1

(hKappa-hu CD45.LC1; Human Kappa)

Signal peptide:

METDTLLLWVLLLWVPGSTG (SEQ ID NO:27)

Light chain variable region:

DIVMTQSPDSLAVSLGERATINCKSSKSVSTSGYSYLHWYQQKPGQPPKLLIYLASNLES
GVPDRFSGSGSGTDFTLTISSLQAEDVAVYYCQHSRELPFTFGQGTKLEIK
(SEQ ID NO:33)

CDR$_{L1}$: KSSKSVSTSGYSYLH (SEQ ID NO:62)

CDR$_{L2}$: LASNLES (SEQ ID NO:60)

CDR$_{L3}$: QHSRELPFT (SEQ ID NO:61)

1$^{st}$ Residue: R    Light chain constant region with 1$^{st}$ Residue: SEQ ID NO:35

Light chain constant region:

TVAAPSVFIFPPSDEQLKSGTASVVCLLNNFYPREAKVQWKVDNALQSGNSQESVTEQD
SKDSTYSLSSTLTLSKADYEKHKVYACEVTHQGLSSPVTKSFNRGEC (SEQ ID NO:34)

Full length light chain including signal peptide:

METDTLLLWVLLLWVPGSTGDIVMTQSPDSLAVSLGERATINCKSSKSVSTSGYSYLHW
YQQKPGQPPKLLIYLASNLESGVPDRFSGSGSGTDFTLTISSLQAEDVAVYYCQHSRELP
FTFGQGTKLEIKRTVAAPSVFIFPPSDEQLKSGTASVVCLLNNFYPREAKVQWKVDNAL
QSGNSQESVTEQDSKDSTYSLSSTLTLSKADYEKHKVYACEVTHQGLSSPVTKSFNRGE
C (SEQ ID NO:36)

Full length light chain without signal peptide: SEQ ID NO:37

FIG. 7 mAb chain ID: hu CD45.LC2

(hKappa-hu CD45.LC2; Human Kappa)

Signal peptide:

METDTLLLWVLLLWVPGSTG (SEQ ID NO:27)

Light chain variable region:

EIVMTQSPATLSLSPGERATLSC<u>RASKSVSTSGYSYLH</u>WYQQKPGQAPRLLIY<u>LASNLAT</u>GIPARFSGSGSGTDFTLTISSLQPEDFAVYYC<u>QHSRELPFT</u>FGQGTKLEIK (SEQ ID NO:38)

CDR$_{L1}$: RASKSVSTSGYSYLH (SEQ ID NO:59)

CDR$_{L2}$: LASNLAT (SEQ ID NO:63)

CDR$_{L3}$: QHSRELPFT (SEQ ID NO:61)

1$^{st}$ Residue: R    Light chain constant region with 1$^{st}$ Residue: SEQ ID NO:40

Light chain constant region:

TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:39)

Full length light chain including signal peptide:

METDTLLLWVLLLWVPGSTGEIVMTQSPATLSLSPGERATLSCRASKSVSTSGYSYLHWYQQKPGQAPRLLIYLASNLATGIPARFSGSGSGTDFTLTISSLQPEDFAVYYCQHSRELPFTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:41)

Full length light chain without signal peptide: SEQ ID NO:42

FIG. 8 mAb chain ID: hu CD45.LC3

(hKappa-hu CD45.LC3; Human Kappa)

Signal peptide:

METDTLLLWVLLLWVPGSTG (SEQ ID NO:27)

Light chain variable region:

EIVLTQSPATLSLSPGERATLSCRASKSVSTSGYSYLHWYQQKPGQAPRLLIYLASNLAT GIPARFSGSGSGTDFTLTISSLEPEDFAVYYCQHSRELPFTFGQGTKLEIK (SEQ ID NO:43)

$CDR_{L1}$: RASKSVSTSGYSYLH (SEQ ID NO:59)

$CDR_{L2}$: LASNLAT (SEQ ID NO:63)

$CDR_{L3}$: QHSRELPFT (SEQ ID NO:61)

$1^{st}$ Residue: R    Light chain constant region with $1^{st}$ Residue: SEQ ID NO:45

Light chain constant region:

TVAAPSVFIFPPSDEQLKSGTASVVCLLNNFYPREAKVQWKVDNALQSGNSQESVTEQD SKDSTYSLSSTLTLSKADYEKHKVYACEVTHQGLSSPVTKSFNRGEC (SEQ ID NO:44)

Full length light chain including signal peptide:

METDTLLLWVLLLWVPGSTGEIVLTQSPATLSLSPGERATLSCRASKSVSTSGYSYLHW YQQKPGQAPRLLIYLASNLATGIPARFSGSGSGTDFTLTISSLEPEDFAVYYCQHSRELPF TFGQGTKLEIKRTVAAPSVFIFPPSDEQLKSGTASVVCLLNNFYPREAKVQWKVDNALQ SGNSQESVTEQDSKDSTYSLSSTLTLSKADYEKHKVYACEVTHQGLSSPVTKSFNRGEC (SEQ ID NO:46)

Full length light chain without signal peptide: SEQ ID NO:47

FIG. 9 mAb chain ID: hu CD45.LC4

(hKappa-hu CD45.LC4; Human Kappa)

Signal peptide:

METDTLLLWVLLLWVPGSTG (SEQ ID NO:27)

Light chain variable region:

DIQMTQSPSSLSASVGDRVTITC<u>RASKSVSTSGYSYLH</u>WYQQKPGKAPKLLIY<u>LASNLQS</u>GVPSRFSGSGSGTDFTLTISSLQPEDFATYYC<u>QHSRELPFT</u>FGQGTKLEIK (SEQ ID NO:48)

CDR<sub>L1</sub>: RASKSVSTSGYSYLH (SEQ ID NO:59)

CDR<sub>L2</sub>: LASNLQS (SEQ ID NO:64)

CDR<sub>L3</sub>: QHSRELPFT (SEQ ID NO:61)

1st Residue: R    Light chain constant region with 1st Residue: SEQ ID NO:50

Light chain constant region:

TVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:49)

Full length light chain including signal peptide:

METDTLLLWVLLLWVPGSTGDIQMTQSPSSLSASVGDRVTITCRASKSVSTSGYSYLHWYQQKPGKAPKLLIYLASNLQSGVPSRFSGSGSGTDFTLTISSLQPEDFATYYCQHSRELPFTFGQGTKLEIKRTVAAPSVFIFPPSDEQLKSGTASVVCLLNNFYPREAKVQWKVDNALQSGNSQESVTEQDSKDSTYSLSSTLTLSKADYEKHKVYACEVTHQGLSSPVTKSFNRGEC (SEQ ID NO:51)

Full length light chain without signal peptide: SEQ ID NO:52

FIG. 10

SEQUENCE LISTING

```
Sequence total quantity: 85
SEQ ID NO: 1             moltype = AA  length = 24
FEATURE                  Location/Qualifiers
REGION                   1..24
                         note = Antibody component sequence
source                   1..24
                         mol_type = protein
                         organism = synthetic construct
SEQUENCE: 1
MDPKGSLSWR ILLFLSLAFE LSYG                                          24

SEQ ID NO: 2             moltype = AA  length = 121
FEATURE                  Location/Qualifiers
REGION                   1..121
                         note = Antibody component sequence
source                   1..121
                         mol_type = protein
                         organism = synthetic construct
SEQUENCE: 2
EVKLLESGGG LVQPGGSLKL SCAASGFDFS RYWMSWVRQA PGKGLEWIGE INPTSSTINF    60
TPSLKDKVFI SRDNAKNTLY LQMSKVRSED TALYYCARGN YYRYGDAMDY WGQGTSVTVS   120
S                                                                  121

SEQ ID NO: 3             moltype = AA  length = 328
FEATURE                  Location/Qualifiers
REGION                   1..328
                         note = Antibody component sequence
source                   1..328
                         mol_type = protein
                         organism = synthetic construct
SEQUENCE: 3
STKGPSVFPL APSSKSTSGG TAALGCLVKD YFPEPVTVSW NSGALTSGVH TFPAVLQSSG    60
LYSLSSVVTV PSSSLGTQTY ICNVNHKPSN TKVDKKVEPK SCDKTHTCPP CPAPELLGGP   120
SVFLFPPKPK DTLMISRTPE VTCVVVDVSH EDPEVKFNWY VDGVEVHNAK TKPREEQYNS   180
TYRVVSVLTV LHQDWLNGKE YKCKVSNKAL PAPIEKTISK AKGQPREPQV YTLPPSREEM   240
TKNQVSLTCL VKGFYPSDIA VEWESNGQPE NNYKTTPPVL DSDGSFFLYS KLTVDKSRWQ   300
QGNVFSCSVM HEALHNHYTQ KSLSLSPG                                     328

SEQ ID NO: 4             moltype = AA  length = 329
FEATURE                  Location/Qualifiers
```

```
REGION                        1..329
                              note = Antibody component sequence
source                        1..329
                              mol_type = protein
                              organism = synthetic construct
SEQUENCE: 4
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 5                  moltype = AA  length = 474
FEATURE                       Location/Qualifiers
source                        1..474
                              mol_type = protein
                              organism = Mus musculus
SEQUENCE: 5
MDPKGSLSWR ILLFLSLAFE LSYGEVKLLE SGGGLVQPGG SLKLSCAASG FDFSRYWMSW   60
VRQAPGKGLE WIGEINPTSS TINFTPSLKD KVFISRDNAK NTLYLQMSKV RSEDTALYYC  120
ARGNYYRYGD AMDYWGQGTS VTVSSASTKG PSVFPPLAPSS KSTGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSREEMTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPG        474

SEQ ID NO: 6                  moltype = AA  length = 450
FEATURE                       Location/Qualifiers
source                        1..450
                              mol_type = protein
                              organism = Mus musculus
SEQUENCE: 6
EVKLLESGGG LVQPGGSLKL SCAASGFDFS RYWMSWVRQA PGKGLEWIGE INPTSSTINF   60
TPSLKDKVFI SRDNAKNTLY LQMSKVRSED TALYYCARGN YYRYGDAMDY WGQGTSVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 7                  moltype = AA  length = 121
FEATURE                       Location/Qualifiers
REGION                        1..121
                              note = Antibody component sequence
source                        1..121
                              mol_type = protein
                              organism = synthetic construct
SEQUENCE: 7
EVQLVESGGG LVQPGGSLRL SCAASGFDFS RYWMSWVRQA PGKGLEWVSE INPTSSTINF   60
ADSVKGRFFI SRDNAKNSLY LQMNSLRAED TAVYYCARGN YYRYGDAMDY WGQGTMVTVS  120
S                                                                 121

SEQ ID NO: 8                  moltype = AA  length = 328
FEATURE                       Location/Qualifiers
REGION                        1..328
                              note = Antibody component sequence
source                        1..328
                              mol_type = protein
                              organism = synthetic construct
SEQUENCE: 8
STKGPSVFPL APSSKSTSGG TAALGCLVKD YFPEPVTVSW NSGALTSGVH TFPAVLQSSG   60
LYSLSSVVTV PSSSLGTQTY ICNVNHKPSN TKVDKKVEPK SCDKTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPG                                    328

SEQ ID NO: 9                  moltype = AA  length = 329
FEATURE                       Location/Qualifiers
REGION                        1..329
                              note = Antibody component sequence
source                        1..329
                              mol_type = protein
                              organism = synthetic construct
SEQUENCE: 9
ASTKGPSVFP LAPSSKSTSG GTAALGCLVK DYFPEPVTVS WNSGALTSGV HTFPAVLQSS   60
```

```
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                  329

SEQ ID NO: 10            moltype = AA  length = 474
FEATURE                  Location/Qualifiers
REGION                   1..474
                         note = Antibody component sequence
source                   1..474
                         mol_type = protein
                         organism = synthetic construct
SEQUENCE: 10
MDPKGSLSWR ILLFLSLAFE LSYGEVQLVE SGGGLVQPGG SLRLSCAASG FDFSRYWMSW   60
VRQAPGKGLE WVSEINPTSS TINFADSVKG RFFISRDNAK NSLYLQMNSL RAEDTAVYYC  120
ARGNYYRYGD AMDYWGQGTM VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSREEMTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPG        474

SEQ ID NO: 11            moltype = AA  length = 450
FEATURE                  Location/Qualifiers
REGION                   1..450
                         note = Antibody component sequence
source                   1..450
                         mol_type = protein
                         organism = synthetic construct
SEQUENCE: 11
EVQLVESGGG LVQPGGSLRL SCAASGFDFS RYWMSWVRQA PGKGLEWVSE INPTSSTINF   60
ADSVKGRFFI SRDNAKNSLY LQMNSLRAED TAVYYCARGN YYRYGDAMDY WGQGTMVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 12            moltype = AA  length = 121
FEATURE                  Location/Qualifiers
REGION                   1..121
                         note = Antibody component sequence
source                   1..121
                         mol_type = protein
                         organism = synthetic construct
SEQUENCE: 12
EVQLLESGGG LVQPGGSLRL SCAASGFDFS RYWMSWVRQA PGKGLEWVSE INPTSSTINY   60
ADSVKGRFTI SRDNSKNTLY LQMNSLRAED TAVYYCARGN YYRYGDAMDY WGQGTMVTVS  120
S                                                                 121

SEQ ID NO: 13            moltype = AA  length = 328
FEATURE                  Location/Qualifiers
REGION                   1..328
                         note = Antibody component sequence
source                   1..328
                         mol_type = protein
                         organism = synthetic construct
SEQUENCE: 13
STKGPSVFPL APSSKSTSGG TAALGCLVKD YFPEPVTVSW NSGALTSGVH TFPAVLQSSG   60
LYSLSSVVTV PSSSLGTQTY ICNVNHKPSN TKVDKKVEPK SCDKTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPG                                    328

SEQ ID NO: 14            moltype = AA  length = 329
FEATURE                  Location/Qualifiers
REGION                   1..329
                         note = Antibody component sequence
source                   1..329
                         mol_type = protein
                         organism = synthetic construct
SEQUENCE: 14
ASTKGPSVFP LAPSSKSTSG GTAALGCLVK DYFPEPVTVS WNSGALTSGV HTFPAVLQSS   60
GLYSLSSVVT VPSSSLGTQT YICNVNHKPS NTKVDKKVEP KSCDKTHTCP PCPAPELLGG  120
PSVFLFPPKP KDTLMISRTP EVTCVVVDVS HEDPEVKFNW YVDGVEVHNA KTKPREEQYN  180
STYRVVSVLT VLHQDWLNGK EYKCKVSNKA LPAPIEKTIS KAKGQPREPQ VYTLPPSREE  240
```

```
MTKNQVSLTC LVKGFYPSDI AVEWESNGQP ENNYKTTPPV LDSDGSFFLY SKLTVDKSRW  300
QQGNVFSCSV MHEALHNHYT QKSLSLSPG                                   329

SEQ ID NO: 15            moltype = AA  length = 474
FEATURE                  Location/Qualifiers
REGION                   1..474
                         note = Antibody component sequence
source                   1..474
                         mol_type = protein
                         organism = synthetic construct
SEQUENCE: 15
MDPKGSLSWR ILLFLSLAFE LSYGEVQLLE SGGGLVQPGG SLRLSCAASG FDFSRYWMSW  60
VRQAPGKGLE WVSEINPTSS TINYADSVKG RFTISRDNSK NTLYLQMNSL RAEDTAVYYC  120
ARGNYYRYGD AMDYWGQGTM VTVSSASTKG PSVFPLAPSS KSTSGGTAAL GCLVKDYFPE  180
PVTVSWNSGA LTSGVHTFPA VLQSSGLYSL SSVVTVPSSS LGTQTYICNV NHKPSNTKVD  240
KKVEPKSCDK THTCPPCPAP ELLGGPSVFL FPPKPKDTLM ISRTPEVTCV VVDVSHEDPE  300
VKFNWYVDGV EVHNAKTKPR EEQYNSTYRV VSVLTVLHQD WLNGKEYKCK VSNKALPAPI  360
EKTISKAKGQ PREPQVYTLP PSREEMTKNQ VSLTCLVKGF YPSDIAVEWE SNGQPENNYK  420
TTPPVLDSDG SFFLYSKLTV DKSRWQQGNV FSCSVMHEAL HNHYTQKSLS LSPG       474

SEQ ID NO: 16            moltype = AA  length = 450
FEATURE                  Location/Qualifiers
REGION                   1..450
                         note = Antibody component sequence
source                   1..450
                         mol_type = protein
                         organism = synthetic construct
SEQUENCE: 16
EVQLLESGGG LVQPGGSLRL SCAASGFDFS RYWMSWVRQA PGKGLEWVSE INPTSSTINY  60
ADSVKGRFTI SRDNSKNTLY LQMNSLRAED TAVYYCARGN YYRYGDAMDY WGQGTMVTVS  120
SASTKGPSVF PLAPSSKSTS GGTAALGCLV KDYFPEPVTV SWNSGALTSG VHTFPAVLQS  180
SGLYSLSSVV TVPSSSLGTQ TYICNVNHKP SNTKVDKKVE PKSCDKTHTC PPCPAPELLG  240
GPSVFLFPPK PKDTLMISRT PEVTCVVVDV SHEDPEVKFN WYVDGVEVHN AKTKPREEQY  300
NSTYRVVSVL TVLHQDWLNG KEYKCKVSNK ALPAPIEKTI SKAKGQPREP QVYTLPPSRE  360
EMTKNQVSLT CLVKGFYPSD IAVEWESNGQ PENNYKTTPP VLDSDGSFFL YSKLTVDKSR  420
WQQGNVFSCS VMHEALHNHY TQKSLSLSPG                                  450

SEQ ID NO: 17            moltype = AA  length = 121
FEATURE                  Location/Qualifiers
REGION                   1..121
                         note = Antibody component sequence
source                   1..121
                         mol_type = protein
                         organism = synthetic construct
SEQUENCE: 17
EVQLVESGGG LVQPGGSLRL SCAASGFDFS RYWMSWVRQA PGKGLEWVAE INPTSSTINF  60
VDSVKGRFTI SRDNAKNSLY LQMNSLRAED TAVYYCARGN YYRYGDAMDY WGQGTMVTVS  120
S                                                                 121

SEQ ID NO: 18            moltype = AA  length = 328
FEATURE                  Location/Qualifiers
REGION                   1..328
                         note = Antibody component sequence
source                   1..328
                         mol_type = protein
                         organism = synthetic construct
SEQUENCE: 18
STKGPSVFPL APSSKSTSGG TAALGCLVKD YFPEPVTVSW NSGALTSGVH TFPAVLQSSG  60
LYSLSSVVTV PSSSLGTQTY ICNVNHKPSN TKVDKKVEPK SCDKTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPG                                    328

SEQ ID NO: 19            moltype = AA  length = 328
FEATURE                  Location/Qualifiers
REGION                   1..328
                         note = Antibody component sequence
source                   1..328
                         mol_type = protein
                         organism = synthetic construct
SEQUENCE: 19
STKGPSVFPL APSSKSTSGG TAALGCLVKD YFPEPVTVSW NSGALTSGVH TFPAVLQSSG  60
LYSLSSVVTV PSSSLGTQTY ICNVNHKPSN TKVDKKVEPK SCDKTHTCPP CPAPELLGGP  120
SVFLFPPKPK DTLMISRTPE VTCVVVDVSH EDPEVKFNWY VDGVEVHNAK TKPREEQYNS  180
TYRVVSVLTV LHQDWLNGKE YKCKVSNKAL PAPIEKTISK AKGQPREPQV YTLPPSREEM  240
TKNQVSLTCL VKGFYPSDIA VEWESNGQPE NNYKTTPPVL DSDGSFFLYS KLTVDKSRWQ  300
QGNVFSCSVM HEALHNHYTQ KSLSLSPG                                    328
```

```
SEQ ID NO: 20              moltype = AA   length = 474
FEATURE                    Location/Qualifiers
REGION                     1..474
                           note = Antibody component sequence
source                     1..474
                           mol_type = protein
                           organism = synthetic construct
SEQUENCE: 20
MDPKGSLSWR ILLFLSLAFE LSYGEVQLVE SGGGLVQPGG SLRLSCAASG FDFSRYWMSW    60
VRQAPGKGLE WVAEINPTSS TINFVDSVKG RFTISRDNAK NSLYLQMNSL RAEDTAVYYC   120
ARGNYYRYGD AMDYWGQGTM VTVSSASTKG PSVFPLAPSS KSTSGGTAAL GCLVKDYFPE   180
PVTVSWNSGA LTSGVHTFPA VLQSSGLYSL SSVVTVPSSS LGTQTYICNV NHKPSNTKVD   240
KKVEPKSCDK THTCPPCPAP ELLGGPSVFL FPPKPKDTLM ISRTPEVTCV VVDVSHEDPE   300
VKFNWYVDGV EVHNAKTKPR EEQYNSTYRV VSVLTVLHQD WLNGKEYKCK VSNKALPAPI   360
EKTISKAKGQ PREPQVYTLP PSREEMTKNQ VSLTCLVKGF YPSDIAVEWE SNGQPENNYK   420
TTPPVLDSDG SFFLYSKLTV DKSRWQQGNV FSCSVMHEAL HNHYTQKSLS LSPG         474

SEQ ID NO: 21              moltype = AA   length = 450
FEATURE                    Location/Qualifiers
REGION                     1..450
                           note = Antibody component sequence
source                     1..450
                           mol_type = protein
                           organism = synthetic construct
SEQUENCE: 21
EVQLVESGGG LVQPGGSLRL SCAASGFDFS RYWMSWVRQA PGKGLEWVAE INPTSSTINF    60
VDSVKGRFTI SRDNAKNSLY LQMNSLRAED TAVYYCARGN YYRYGDAMDY WGQGTMVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                    450

SEQ ID NO: 22              moltype = AA   length = 121
FEATURE                    Location/Qualifiers
REGION                     1..121
                           note = Antibody component sequence
source                     1..121
                           mol_type = protein
                           organism = synthetic construct
SEQUENCE: 22
EVQLVESGGG LVKPGGSLRL SCAASGFDFS RYWMSWVRQA PGKGLEWVSE INPTSSTINY    60
ADSVKGRFTI SRDNAKNSLY LQMNSLRAED TAVYYCARGN YYRYGDAMDY WGQGTMVTVS   120
S                                                                   121

SEQ ID NO: 23              moltype = AA   length = 328
FEATURE                    Location/Qualifiers
REGION                     1..328
                           note = Antibody component sequence
source                     1..328
                           mol_type = protein
                           organism = synthetic construct
SEQUENCE: 23
STKGPSVFPL APSSKSTSGG TAALGCLVKD YFPEPVTVSW NSGALTSGVH TFPAVLQSSG    60
LYSLSSVVTV PSSSLGTQTY ICNVNHKPSN TKVDKKVEPK SCDKTHTCPP CPAPELLGGP   120
SVFLFPPKPK DTLMISRTPE VTCVVVDVSH EDPEVKFNWY VDGVEVHNAK TKPREEQYNS   180
TYRVVSVLTV LHQDWLNGKE YKCKVSNKAL PAPIEKTISK AKGQPREPQV YTLPPSREEM   240
TKNQVSLTCL VKGFYPSDIA VEWESNGQPE NNYKTTPPVL DSDGSFFLYS KLTVDKSRWQ   300
QGNVFSCSVM HEALHNHYTQ KSLSLSPG                                      328

SEQ ID NO: 24              moltype = AA   length = 329
FEATURE                    Location/Qualifiers
REGION                     1..329
                           note = Antibody component sequence
source                     1..329
                           mol_type = protein
                           organism = synthetic construct
SEQUENCE: 24
ASTKGPSVFP LAPSSKSTSG GTAALGCLVK DYFPEPVTVS WNSGALTSGV HTFPAVLQSS    60
GLYSLSSVVT VPSSSLGTQT YICNVNHKPS NTKVDKKVEP KSCDKTHTCP PCPAPELLGG   120
PSVFLFPPKP KDTLMISRTP EVTCVVVDVS HEDPEVKFNW YVDGVEVHNA KTKPREEQYN   180
STYRVVSVLT VLHQDWLNGK EYKCKVSNKA LPAPIEKTIS KAKGQPREPQ VYTLPPSREE   240
MTKNQVSLTC LVKGFYPSDI AVEWESNGQP ENNYKTTPPV LDSDGSFFLY SKLTVDKSRW   300
QQGNVFSCSV MHEALHNHYT QKSLSLSPG                                     329

SEQ ID NO: 25              moltype = AA   length = 474
FEATURE                    Location/Qualifiers
REGION                     1..474
```

```
                              note = Antibody component sequence
source                        1..474
                              mol_type = protein
                              organism = synthetic construct
SEQUENCE: 25
MDPKGSLSWR ILLFLSLAFE LSYGEVQLVE SGGGLVKPGG SLRLSCAASG FDFSRYWMSW    60
VRQAPGKGLE WVSEINPTSS TINYADSVKG RFTISRDNAK NSLYLQMNSL RAEDTAVYYC   120
ARGNYYRYGD AMDYWGQGTM VTVSSASTKG PSVFPLAPSS KSTSGGTAAL GCLVKDYFPE   180
PVTVSWNSGA LTSGVHTFPA VLQSSGLYSL SSVVTVPSSS LGTQTYICNV NHKPSNTKVD   240
KKVEPKSCDK THTCPPCPAP ELLGGPSVFL FPPKPKDTLM ISRTPEVTCV VVDVSHEDPE   300
VKFNWYVDGV EVHNAKTKPR EEQYNSTYRV VSVLTVLHQD WLNGKEYKCK VSNKALPAPI   360
EKTISKAKGQ PREPQVYTLP PSREEMTKNQ VSLTCLVKGF YPSDIAVEWE SNGQPENNYK   420
TTPPVLDSDG SFFLYSKLTV DKSRWQQGNV FSCSVMHEAL HNHYTQKSLS LSPG         474

SEQ ID NO: 26               moltype = AA   length = 450
FEATURE                     Location/Qualifiers
REGION                      1..450
                              note = Antibody component sequence
source                        1..450
                              mol_type = protein
                              organism = synthetic construct
SEQUENCE: 26
EVQLVESGGG LVKPGGSLRL SCAASGFDFS RYWMSWVRQA PGKGLEWVSE INPTSSTINY    60
ADSVKGRFTI SRDNAKNSLY LQMNSLRAED TAVYYCARGN YYRYGDAMDY WGQGTMVTVS   120
SASTKGPSVF PLAPSSKSTS GGTAALGCLV KDYFPEPVTV SWNSGALTSG VHTFPAVLQS   180
SGLYSLSSVV TVPSSSLGTQ TYICNVNHKP SNTKVDKKVE PKSCDKTHTC PPCPAPELLG   240
GPSVFLFPPK PKDTLMISRT PEVTCVVVDV SHEDPEVKFN WYVDGVEVHN AKTKPREEQY   300
NSTYRVVSVL TVLHQDWLNG KEYKCKVSNK ALPAPIEKTI SKAKGQPREP QVYTLPPSRE   360
EMTKNQVSLT CLVKGFYPSD IAVEWESNGQ PENNYKTTPP VLDSDGSFFL YSKLTVDKSR   420
WQQGNVFSCS VMHEALHNHY TQKSLSLSPG                                    450

SEQ ID NO: 27               moltype = AA   length = 20
FEATURE                     Location/Qualifiers
REGION                      1..20
                              note = Antibody component sequence
source                        1..20
                              mol_type = protein
                              organism = synthetic construct
SEQUENCE: 27
METDTLLLWV LLLWVPGSTG                                                20

SEQ ID NO: 28               moltype = AA   length = 111
FEATURE                     Location/Qualifiers
REGION                      1..111
                              note = Antibody component sequence
source                        1..111
                              mol_type = protein
                              organism = synthetic construct
SEQUENCE: 28
DIALTQSPAS LAVSLGQRAT ISCRASKSVS TSGYSYLHWY QQKPGQPPKL LIYLASNLES    60
GVPARFSGSG SGTDFTLNIH PVEEEDAATY YCQHSRELPF TFGSGTKLEI K            111

SEQ ID NO: 29               moltype = AA   length = 106
FEATURE                     Location/Qualifiers
REGION                      1..106
                              note = Antibody component sequence
source                        1..106
                              mol_type = protein
                              organism = synthetic construct
SEQUENCE: 29
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                  106

SEQ ID NO: 30               moltype = AA   length = 107
FEATURE                     Location/Qualifiers
REGION                      1..107
                              note = Antibody component sequence
source                        1..107
                              mol_type = protein
                              organism = synthetic construct
SEQUENCE: 30
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 31               moltype = AA   length = 238
FEATURE                     Location/Qualifiers
source                        1..238
                              mol_type = protein
                              organism = Mus musculus
```

```
SEQUENCE: 31
METDTLLLWV LLLWVPGSTG DIALTQSPAS LAVSLGQRAT ISCRASKSVS TSGYSYLHWY    60
QQKPGQPPKL LIYLASNLES GVPARFSGSG SGTDFTLNIH PVEEEDAATY YCQHSRELPF   120
TFGSGTKLEI KRTVAAPSVF IFPPSDEQLK SGTASVVCLL NNFYPREAKV QWKVDNALQS   180
GNSQESVTEQ DSKDSTYSLS STLTLSKADY EKHKVYACEV THQGLSSPVT KSFNRGEC     238

SEQ ID NO: 32           moltype = AA   length = 218
FEATURE                 Location/Qualifiers
source                  1..218
                        mol_type = protein
                        organism = Mus musculus
SEQUENCE: 32
DIALTQSPAS LAVSLGQRAT ISCRASKSVS TSGYSYLHWY QQKPGQPPKL LIYLASNLES    60
GVPARFSGSG SGTDFTLNIH PVEEEDAATY YCQHSRELPF TFGSGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 33           moltype = AA   length = 111
FEATURE                 Location/Qualifiers
REGION                  1..111
                        note = Antibody component sequence
source                  1..111
                        mol_type = protein
                        organism = synthetic construct
SEQUENCE: 33
DIVMTQSPDS LAVSLGERAT INCKSSKSVS TSGYSYLHWY QQKPGQPPKL LIYLASNLES    60
GVPDRFSGSG SGTDFTLTIS SLQAEDVAVY YCQHSRELPF TFGQGTKLEI K            111

SEQ ID NO: 34           moltype = AA   length = 106
FEATURE                 Location/Qualifiers
REGION                  1..106
                        note = Antibody component sequence
source                  1..106
                        mol_type = protein
                        organism = synthetic construct
SEQUENCE: 34
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                  106

SEQ ID NO: 35           moltype = AA   length = 107
FEATURE                 Location/Qualifiers
REGION                  1..107
                        note = Antibody component sequence
source                  1..107
                        mol_type = protein
                        organism = synthetic construct
SEQUENCE: 35
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                 107

SEQ ID NO: 36           moltype = AA   length = 238
FEATURE                 Location/Qualifiers
REGION                  1..238
                        note = Antibody component sequence
source                  1..238
                        mol_type = protein
                        organism = synthetic construct
SEQUENCE: 36
METDTLLLWV LLLWVPGSTG DIVMTQSPDS LAVSLGERAT INCKSSKSVS TSGYSYLHWY    60
QQKPGQPPKL LIYLASNLES GVPDRFSGSG SGTDFTLTIS SLQAEDVAVY YCQHSRELPF   120
TFGQGTKLEI KRTVAAPSVF IFPPSDEQLK SGTASVVCLL NNFYPREAKV QWKVDNALQS   180
GNSQESVTEQ DSKDSTYSLS STLTLSKADY EKHKVYACEV THQGLSSPVT KSFNRGEC     238

SEQ ID NO: 37           moltype = AA   length = 218
FEATURE                 Location/Qualifiers
REGION                  1..218
                        note = Antibody component sequence
source                  1..218
                        mol_type = protein
                        organism = synthetic construct
SEQUENCE: 37
DIVMTQSPDS LAVSLGERAT INCKSSKSVS TSGYSYLHWY QQKPGQPPKL LIYLASNLES    60
GVPDRFSGSG SGTDFTLTIS SLQAEDVAVY YCQHSRELPF TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 38           moltype = AA   length = 111
FEATURE                 Location/Qualifiers
REGION                  1..111
```

```
                        note = Antibody component sequence
source                  1..111
                        mol_type = protein
                        organism = synthetic construct
SEQUENCE: 38
EIVMTQSPAT LSLSPGERAT LSCRASKSVS TSGYSYLHWY QQKPGQAPRL LIYLASNLAT    60
GIPARFSGSG SGTDFTLTIS SLQPEDFAVY YCQHSRELPF TFGQGTKLEI K            111

SEQ ID NO: 39           moltype = AA  length = 106
FEATURE                 Location/Qualifiers
REGION                  1..106
                        note = Antibody component sequence
source                  1..106
                        mol_type = protein
                        organism = synthetic construct
SEQUENCE: 39
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 40           moltype = AA  length = 107
FEATURE                 Location/Qualifiers
REGION                  1..107
                        note = Antibody component sequence
source                  1..107
                        mol_type = protein
                        organism = synthetic construct
SEQUENCE: 40
RTVAAPSVFI FPPSDEQLKS GTASVVCLLN NFYPREAKVQ WKVDNALQSG NSQESVTEQD    60
SKDSTYSLSS TLTLSKADYE KHKVYACEVT HQGLSSPVTK SFNRGEC                107

SEQ ID NO: 41           moltype = AA  length = 238
FEATURE                 Location/Qualifiers
REGION                  1..238
                        note = Antibody component sequence
source                  1..238
                        mol_type = protein
                        organism = synthetic construct
SEQUENCE: 41
METDTLLLWV LLLWVPGSTG EIVMTQSPAT LSLSPGERAT LSCRASKSVS TSGYSYLHWY    60
QQKPGQAPRL LIYLASNLAT GIPARFSGSG SGTDFTLTIS SLQPEDFAVY YCQHSRELPF   120
TFGQGTKLEI KRTVAAPSVF IFPPSDEQLK SGTASVVCLL NNFYPREAKV QWKVDNALQS   180
GNSQESVTEQ DSKDSTYSLS STLTLSKADY EKHKVYACEV THQGLSSPVT KSFNRGEC     238

SEQ ID NO: 42           moltype = AA  length = 218
FEATURE                 Location/Qualifiers
REGION                  1..218
                        note = Antibody component sequence
source                  1..218
                        mol_type = protein
                        organism = synthetic construct
SEQUENCE: 42
EIVMTQSPAT LSLSPGERAT LSCRASKSVS TSGYSYLHWY QQKPGQAPRL LIYLASNLAT    60
GIPARFSGSG SGTDFTLTIS SLQPEDFAVY YCQHSRELPF TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                          218

SEQ ID NO: 43           moltype = AA  length = 111
FEATURE                 Location/Qualifiers
REGION                  1..111
                        note = Antibody component sequence
source                  1..111
                        mol_type = protein
                        organism = synthetic construct
SEQUENCE: 43
EIVLTQSPAT LSLSPGERAT LSCRASKSVS TSGYSYLHWY QQKPGQAPRL LIYLASNLAT    60
GIPARFSGSG SGTDFTLTIS SLEPEDFAVY YCQHSRELPF TFGQGTKLEI K            111

SEQ ID NO: 44           moltype = AA  length = 106
FEATURE                 Location/Qualifiers
REGION                  1..106
                        note = Antibody component sequence
source                  1..106
                        mol_type = protein
                        organism = synthetic construct
SEQUENCE: 44
TVAAPSVFIF PPSDEQLKSG TASVVCLLNN FYPREAKVQW KVDNALQSGN SQESVTEQDS    60
KDSTYSLSST LTLSKADYEK HKVYACEVTH QGLSSPVTKS FNRGEC                 106

SEQ ID NO: 45           moltype = AA  length = 107
```

```
FEATURE                 Location/Qualifiers
REGION                  1..107
                        note = Antibody component sequence
source                  1..107
                        mol_type = protein
                        organism = synthetic construct
SEQUENCE: 45
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 46           moltype = AA  length = 238
FEATURE                 Location/Qualifiers
REGION                  1..238
                        note = Antibody component sequence
source                  1..238
                        mol_type = protein
                        organism = synthetic construct
SEQUENCE: 46
METDTLLLWV LLLWVPGSTG EIVLTQSPAT LSLSPGERAT LSCRASKSVS TSGYSYLHWY   60
QQKPGQAPRL LIYLASNLAT GIPARFSGSG SGTDFTLTIS SLEPEDFAVY YCQHSRELPF  120
TFGQGTKLEI KRTVAAPSVF IFPPSDEQLK SGTASVVCLL NNFYPREAKV QWKVDNALQS  180
GNSQESVTEQ DSKDSTYSLS STLTLSKADY EKHKVYACEV THQGLSSPVT KSFNRGEC    238

SEQ ID NO: 47           moltype = AA  length = 218
FEATURE                 Location/Qualifiers
REGION                  1..218
                        note = Antibody component sequence
source                  1..218
                        mol_type = protein
                        organism = synthetic construct
SEQUENCE: 47
EIVLTQSPAT LSLSPGERAT LSCRASKSVS TSGYSYLHWY QQKPGQAPRL LIYLASNLAT   60
GIPARFSGSG SGTDFTLTIS SLEPEDFAVY YCQHSRELPF TFGQGTKLEI KRTVAAPSVF  120
IFPPSDEQLK SGTASVVCLL NNFYPREAKV QWKVDNALQS GNSQESVTEQ DSKDSTYSLS  180
STLTLSKADY EKHKVYACEV THQGLSSPVT KSFNRGEC                          218

SEQ ID NO: 48           moltype = AA  length = 111
FEATURE                 Location/Qualifiers
REGION                  1..111
                        note = Antibody component sequence
source                  1..111
                        mol_type = protein
                        organism = synthetic construct
SEQUENCE: 48
DIQMTQSPSS LSASVGDRVT ITCRASKSVS TSGYSYLHWY QQKPGKAPKL LIYLASNLQS   60
GVPSRFSGSG SGTDFTLTIS SLQPEDFATY YCQHSRELPF TFGQGTKLEI K           111

SEQ ID NO: 49           moltype = AA  length = 106
FEATURE                 Location/Qualifiers
REGION                  1..106
                        note = Antibody component sequence
source                  1..106
                        mol_type = protein
                        organism = synthetic construct
SEQUENCE: 49
TVAAPSVFIF PPSDEQLKSG TASVVCLLNN FYPREAKVQW KVDNALQSGN SQESVTEQDS   60
KDSTYSLSST LTLSKADYEK HKVYACEVTH QGLSSPVTKS FNRGEC                 106

SEQ ID NO: 50           moltype = AA  length = 107
FEATURE                 Location/Qualifiers
REGION                  1..107
                        note = Antibody component sequence
source                  1..107
                        mol_type = protein
                        organism = synthetic construct
SEQUENCE: 50
RTVAAPSVFI FPPSDEQLKS GTASVVCLLN NFYPREAKVQ WKVDNALQSG NSQESVTEQD   60
SKDSTYSLSS TLTLSKADYE KHKVYACEVT HQGLSSPVTK SFNRGEC                107

SEQ ID NO: 51           moltype = AA  length = 238
FEATURE                 Location/Qualifiers
REGION                  1..238
                        note = Antibody component sequence
source                  1..238
                        mol_type = protein
                        organism = synthetic construct
SEQUENCE: 51
METDTLLLWV LLLWVPGSTG DIQMTQSPSS LSASVGDRVT ITCRASKSVS TSGYSYLHWY   60
QQKPGKAPKL LIYLASNLQS GVPSRFSGSG SGTDFTLTIS SLQPEDFATY YCQHSRELPF  120
```

```
TFGQGTKLEI KRTVAAPSVF IFPPSDEQLK SGTASVVCLL NNFYPREAKV QWKVDNALQS    180
GNSQESVTEQ DSKDSTYSLS STLTLSKADY EKHKVYACEV THQGLSSPVT KSFNRGEC      238

SEQ ID NO: 52            moltype = AA   length = 218
FEATURE                  Location/Qualifiers
REGION                   1..218
                         note = Antibody component sequence
source                   1..218
                         mol_type = protein
                         organism = synthetic construct
SEQUENCE: 52
DIQMTQSPSS LSASVGDRVT ITCRASKSVS TSGYSYLHWY QQKPGKAPKL LIYLASNLQS    60
GVPSRFSGSG SGTDFTLTIS SLQPEDFATY YCQHSRELPF TFGQGTKLEI KRTVAAPSVF   120
IFPPSDEQLK SGTASVVCLL NNFYPREAKV QWKVDNALQS GNSQESVTEQ DSKDSTYSLS   180
STLTLSKADY EKHKVYACEV THQGLSSPVT KSFNRGEC                           218

SEQ ID NO: 53            moltype = AA   length = 10
FEATURE                  Location/Qualifiers
REGION                   1..10
                         note = Antibody component sequence
source                   1..10
                         mol_type = protein
                         organism = synthetic construct
SEQUENCE: 53
GFDFSRYWMS                                                           10

SEQ ID NO: 54            moltype = AA   length = 17
FEATURE                  Location/Qualifiers
REGION                   1..17
                         note = Antibody component sequence
source                   1..17
                         mol_type = protein
                         organism = synthetic construct
SEQUENCE: 54
EINPTSSTIN FTPSLKD                                                   17

SEQ ID NO: 55            moltype = AA   length = 12
FEATURE                  Location/Qualifiers
REGION                   1..12
                         note = Antibody component sequence
source                   1..12
                         mol_type = protein
                         organism = synthetic construct
SEQUENCE: 55
GNYYRYGDAM DY                                                        12

SEQ ID NO: 56            moltype = AA   length = 17
FEATURE                  Location/Qualifiers
REGION                   1..17
                         note = Antibody component sequence
source                   1..17
                         mol_type = protein
                         organism = synthetic construct
SEQUENCE: 56
EINPTSSTIN FADSVKG                                                   17

SEQ ID NO: 57            moltype = AA   length = 17
FEATURE                  Location/Qualifiers
REGION                   1..17
                         note = Antibody component sequence
source                   1..17
                         mol_type = protein
                         organism = synthetic construct
SEQUENCE: 57
EINPTSSTIN YADSVKG                                                   17

SEQ ID NO: 58            moltype = AA   length = 17
FEATURE                  Location/Qualifiers
REGION                   1..17
                         note = Antibody component sequence
source                   1..17
                         mol_type = protein
                         organism = synthetic construct
SEQUENCE: 58
EINPTSSTIN FVDSVKG                                                   17

SEQ ID NO: 59            moltype = AA   length = 15
FEATURE                  Location/Qualifiers
REGION                   1..15
```

```
                       note = Antibody component sequence
source                 1..15
                       mol_type = protein
                       organism = synthetic construct
SEQUENCE: 59
RASKSVSTSG YSYLH                                                         15

SEQ ID NO: 60          moltype = AA  length = 7
FEATURE                Location/Qualifiers
REGION                 1..7
                       note = Antibody component sequence
source                 1..7
                       mol_type = protein
                       organism = synthetic construct
SEQUENCE: 60
LASNLES                                                                   7

SEQ ID NO: 61          moltype = AA  length = 9
FEATURE                Location/Qualifiers
REGION                 1..9
                       note = Antibody component sequence
source                 1..9
                       mol_type = protein
                       organism = synthetic construct
SEQUENCE: 61
QHSRELPFT                                                                 9

SEQ ID NO: 62          moltype = AA  length = 15
FEATURE                Location/Qualifiers
REGION                 1..15
                       note = Antibody component sequence
source                 1..15
                       mol_type = protein
                       organism = synthetic construct
SEQUENCE: 62
KSSKSVSTSG YSYLH                                                         15

SEQ ID NO: 63          moltype = AA  length = 7
FEATURE                Location/Qualifiers
REGION                 1..7
                       note = Antibody component sequence
source                 1..7
                       mol_type = protein
                       organism = synthetic construct
SEQUENCE: 63
LASNLAT                                                                   7

SEQ ID NO: 64          moltype = AA  length = 7
FEATURE                Location/Qualifiers
REGION                 1..7
                       note = Antibody component sequence
source                 1..7
                       mol_type = protein
                       organism = synthetic construct
SEQUENCE: 64
LASNLQS                                                                   7

SEQ ID NO: 65          moltype = AA  length = 15
FEATURE                Location/Qualifiers
REGION                 1..15
                       note = Antibody component sequence
source                 1..15
                       mol_type = protein
                       organism = synthetic construct
SEQUENCE: 65
RASKSVSTSG YSYLA                                                         15

SEQ ID NO: 66          moltype = AA  length = 15
FEATURE                Location/Qualifiers
REGION                 1..15
                       note = Antibody component sequence
source                 1..15
                       mol_type = protein
                       organism = synthetic construct
SEQUENCE: 66
RASKSVSTSG YSYLS                                                         15

SEQ ID NO: 67          moltype = AA  length = 15
FEATURE                Location/Qualifiers
```

```
REGION                  1..15
                        note = Antibody component sequence
source                  1..15
                        mol_type = protein
                        organism = synthetic construct
SEQUENCE: 67
RASKSVSTSG YSYLN                                                             15

SEQ ID NO: 68           moltype = AA   length = 6
FEATURE                 Location/Qualifiers
REGION                  1..6
                        note = Antibody component sequence
source                  1..6
                        mol_type = protein
                        organism = synthetic construct
SEQUENCE: 68
LASNLA                                                                        6

SEQ ID NO: 69           moltype = AA   length = 6
FEATURE                 Location/Qualifiers
REGION                  1..6
                        note = Antibody component sequence
source                  1..6
                        mol_type = protein
                        organism = synthetic construct
SEQUENCE: 69
LASNLQ                                                                        6

SEQ ID NO: 70           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 70
LASTRES                                                                       7

SEQ ID NO: 71           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 71
LASTRAT                                                                       7

SEQ ID NO: 72           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 72
LASNRAT                                                                       7

SEQ ID NO: 73           moltype = AA   length = 7
FEATURE                 Location/Qualifiers
REGION                  1..7
                        note = Antibody component sequence
source                  1..7
                        mol_type = protein
                        organism = synthetic construct
SEQUENCE: 73
LASSQLS                                                                       7

SEQ ID NO: 74           moltype = AA   length = 17
FEATURE                 Location/Qualifiers
REGION                  1..17
                        note = Antibody component sequence
source                  1..17
                        mol_type = protein
                        organism = synthetic construct
SEQUENCE: 74
YINPTSSTIY YADSVKG                                                           17

SEQ ID NO: 75           moltype = AA   length = 17
```

| FEATURE | Location/Qualifiers |
|---|---|
| REGION | 1..17 |
| | note = Antibody component sequence |
| source | 1..17 |
| | mol_type = protein |
| | organism = synthetic construct |

SEQUENCE: 75
AINPTSSTIY YADSVKG                                                17

| SEQ ID NO: 76 | moltype = AA   length = 17 |
|---|---|
| FEATURE | Location/Qualifiers |
| REGION | 1..17 |
| | note = Antibody component sequence |
| source | 1..17 |
| | mol_type = protein |
| | organism = synthetic construct |

SEQUENCE: 76
NINPTSSTIY YVDSVKG                                                17

| SEQ ID NO: 77 | moltype = AA   length = 17 |
|---|---|
| FEATURE | Location/Qualifiers |
| REGION | 1..17 |
| | note = Antibody component sequence |
| source | 1..17 |
| | mol_type = protein |
| | organism = synthetic construct |

SEQUENCE: 77
SINPTSSTIY YADSVKG                                                17

| SEQ ID NO: 78 | moltype = AA   length = 121 |
|---|---|
| FEATURE | Location/Qualifiers |
| REGION | 1..121 |
| | note = Antibody component sequence |
| SITE | 35 |
| | note = misc_feature - Xaa can be any naturally occurring amino acid |
| REGION | 48..50 |
| | note = misc_feature - Xaa can be any naturally occurring amino acid |
| REGION | 59..62 |
| | note = misc_feature - Xaa can be any naturally occurring amino acid |
| REGION | 66..69 |
| | note = misc_feature - Xaa can be any naturally occurring amino acid |
| SITE | 75 |
| | note = misc_feature - Xaa can be any naturally occurring amino acid |
| SITE | 78 |
| | note = misc_feature - Xaa can be any naturally occurring amino acid |
| REGION | 85..86 |
| | note = misc_feature - Xaa can be any naturally occurring amino acid |
| SITE | 88 |
| | note = misc_feature - Xaa can be any naturally occurring amino acid |
| SITE | 93 |
| | note = misc_feature - Xaa can be any naturally occurring amino acid |
| SITE | 116 |
| | note = misc_feature - Xaa can be any naturally occurring amino acid |
| source | 1..121 |
| | mol_type = protein |
| | organism = synthetic construct |

SEQUENCE: 78
EVKLLESGGG LVQPGGSLKL SCAASGFDFS RYWMXWVRQA PGKGLEWXXX INPTSSTIXX    60
XXSLKXXXXI SRDNXKNXLY LQMSXXRXED TAXYYCARGN YYRYGDAMDY WGQGTXVTVS  120
S                                                                121

| SEQ ID NO: 79 | moltype = AA   length = 111 |
|---|---|
| FEATURE | Location/Qualifiers |
| REGION | 1..111 |
| | note = Antibody component sequence |
| REGION | 3..4 |
| | note = misc_feature - Xaa can be any naturally occurring amino acid |
| REGION | 9..10 |

```
                        note = misc_feature - Xaa can be any naturally occurring
                            amino acid
REGION                  12..13
                        note = misc_feature - Xaa can be any naturally occurring
                            amino acid
SITE                    15
                        note = misc_feature - Xaa can be any naturally occurring
                            amino acid
SITE                    17
                        note = misc_feature - Xaa can be any naturally occurring
                            amino acid
SITE                    19
                        note = misc_feature - Xaa can be any naturally occurring
                            amino acid
REGION                  21..22
                        note = misc_feature - Xaa can be any naturally occurring
                            amino acid
REGION                  24..25
                        note = misc_feature - Xaa can be any naturally occurring
                            amino acid
SITE                    38
                        note = misc_feature - Xaa can be any naturally occurring
                            amino acid
SITE                    47
                        note = misc_feature - Xaa can be any naturally occurring
                            amino acid
SITE                    49
                        note = misc_feature - Xaa can be any naturally occurring
                            amino acid
REGION                  57..60
                        note = misc_feature - Xaa can be any naturally occurring
                            amino acid
SITE                    62
                        note = misc_feature - Xaa can be any naturally occurring
                            amino acid
SITE                    64
                        note = misc_feature - Xaa can be any naturally occurring
                            amino acid
SITE                    78
                        note = misc_feature - Xaa can be any naturally occurring
                            amino acid
REGION                  80..84
                        note = misc_feature - Xaa can be any naturally occurring
                            amino acid
SITE                    87
                        note = misc_feature - Xaa can be any naturally occurring
                            amino acid
SITE                    89
                        note = misc_feature - Xaa can be any naturally occurring
                            amino acid
SITE                    104
                        note = misc_feature - Xaa can be any naturally occurring
                            amino acid
source                  1..111
                        mol_type = protein
                        organism = synthetic construct
SEQUENCE: 79
DIXXTQSPXX LXXSXGXRXT XXCXXSKSVS TSGYSYLXWY QQKPGQXPXL LIYLASXXXX          60
GXPXRFSGSG SGTDFTLXIX XXXXEDXAXY YCQHSRELPF TFGXGTKLEI K                  111

SEQ ID NO: 80           moltype = AA   length = 29
FEATURE                 Location/Qualifiers
REGION                  1..29
                        note = Antibody component sequence
source                  1..29
                        mol_type = protein
                        organism = synthetic construct
SEQUENCE: 80
KISGGGGSGG GGSGGGGSGG GGSGGGGSS                                           29

SEQ ID NO: 81           moltype = AA   length = 21
FEATURE                 Location/Qualifiers
REGION                  1..21
                        note = Antibody component sequence
source                  1..21
                        mol_type = protein
                        organism = synthetic construct
SEQUENCE: 81
SPNSASHSGS APQTSSAPGS Q                                                   21
```

```
SEQ ID NO: 82            moltype = AA  length = 16
FEATURE                  Location/Qualifiers
REGION                   1..16
                         note = Antibody component sequence
source                   1..16
                         mol_type = protein
                         organism = synthetic construct
SEQUENCE: 82
GGGSGGGSGG GSGGGS                                                             16

SEQ ID NO: 83            moltype = AA  length = 5
FEATURE                  Location/Qualifiers
REGION                   1..5
                         note = Antibody component sequence
source                   1..5
                         mol_type = protein
                         organism = synthetic construct
SEQUENCE: 83
GGGGS                                                                          5

SEQ ID NO: 84            moltype = AA  length = 25
FEATURE                  Location/Qualifiers
REGION                   1..25
                         note = Antibody component sequence
source                   1..25
                         mol_type = protein
                         organism = synthetic construct
SEQUENCE: 84
GGGGSGGGGS GGGGSGGGGS GGGGS                                                   25

SEQ ID NO: 85            moltype = AA  length = 10
FEATURE                  Location/Qualifiers
REGION                   1..10
                         note = Antibody component sequence
source                   1..10
                         mol_type = protein
                         organism = synthetic construct
SEQUENCE: 85
GFDFSRYWMN                                                                    10
```

HUMANIZED ANTI-CD45 ANTIBODIES

CROSS-REFERENCE TO RELATED APPLICATIONS

This application is a continuation-in-part of International application no. PCT/US2023/064941 filed Mar. 24, 2023, which claims priority to U.S. provisional application Ser. No. 63/407,979 filed Sep. 19, 2022, U.S. provisional application Ser. No. 63/405,237 filed Sep. 9, 2022, and U.S. provisional application Ser. No. 63/323,257 filed Mar. 24, 2022, each of which is hereby incorporated by reference in its entirety.

SEQUENCE LISTING

The instant application contains a Sequence Listing which has been submitted electronically in XML format and is hereby incorporated by reference in its entirety. Said XML copy, created on Sep. 11, 2023, is named ATNM-016PCT-CIP_SL_ST26.xml and is 130,420 bytes in size.

FIELD OF THE INVENTION

The invention relates to the field of antibody-based therapeutics.

BACKGROUND

The CD45 antigen is a member of the protein tyrosine phosphatase (PTP) family and is a 180-240 kD transmembrane glycoprotein. It is also known as the leukocyte common antigen (LCA), T200, or Ly-5. CD45 plays a key role in T-cell and B-cells receptor signal transduction. Different isoforms of CD45 exist due to variable splicing of its exons. These isoforms are very specific to the activation and maturation state of the cell as well as cell type. The various isoforms have the same trans-membrane and cytoplasmic segments, but different extra-cellular domains, and are differentially expressed on subpopulations of B- and T-cell lymphocytes. The primary ligands described for CD45 include galectin-1, CD1, CD2, CD3, CD4, TCR, CD22 and Thy-1.

Monoclonal antibodies (mAbs) restricted in their specificity to one or the other isoforms of CD45 have been identified, as well as mAbs recognizing an epitope common to all CD45 isoforms. The mAbs designated CD45RA recognize the product of exon-A. The mAbs designated CD45RB recognize the product of exon-B. The mAbs designated CD45RO (as exemplified by UCHL1) selectively bind to the 180 kD isoform (without any of the variable exons A, B or C) which is restricted to a subset of cortical thymocytes, activated T cells and memory cells, and is absent on B cells. BC8, also known as apamistamab, is a murine IgG1 monoclonal antibody that recognizes all isoforms of human CD45.

Cells of hematopoietic origin, except mature erythrocytes and platelets, generally express CD45. High expression of CD45 is seen with most acute lymphoid and myeloid leukemias. Since CD45 is not found on tissues of non-hematopoietic origin, its specific expression in leukemia has made it a good target for developing therapeutics, including radio-immunotheraputics. For example, CD45 is expressed at a density of approximately 200,000 to 300,000 sites per cell on circulating leukocytes and malignant B cells.

What is needed and provided by the various aspects of the present invention are new humanized antibodies against human CD45.

SUMMARY OF THE INVENTION

One aspect of the invention provides an anti-huCD45 antibody, comprising:
  (i) a heavy chain which is mCD45-HC parental, huCD45.HC1, huCD45.HC2, huCD45.HC3, huCD45.HC1, or huCD45.HC4, or any of said heavy chains without the signal sequence, or a heavy chain comprising the heavy chain variable region of any of said heavy chains; and
  (ii) a light chain which is mCD45-LC parental, huCD45.LC1, huCD45.LC2, huCD45.LC3, or huCD45.LC4, or any of said light chains without the signal sequence, or a light chain comprising the light chain variable region of any of said light chains,
  provided that when the heavy chain is mCD45-HC parental with or without the signal sequence, the light chain is not mCD45-LC parental with or without the signal sequence, or a human CD45-binding fragment of the antibody, such as a Fab fragment or Fab$_2$ fragment or a corresponding scFv molecule.

A related aspect of the invention provides an anti-huCD45 antibody or a human CD45-binding antibody fragment, including:
  (i) an immunoglobulin heavy chain variable region including SEQ ID NO:2 (from mCD45-HC parental), SEQ ID NO:7 (from huCD45.HC1), SEQ ID NO:12 (from huCD45.HC2), SEQ ID NO:17 (from huCD45.HC3), or SEQ ID NO:22 (from huCD45.HC4); and
  (ii) an immunoglobulin light chain variable region including SEQ ID NO:28 (from mCD45-LC parental), SEQ ID NO:33 (from huCD45.LC1), SEQ ID NO:38 (from huCD45.LC2), SEQ ID NO:43 (from huCD45.LC3), or SEQ ID NO:48 (from huCD45.LC4),
  provided that when the heavy chain variable region includes SEQ ID NO:2, the light chain variable region is not SEQ ID NO:28.

In a variation of the preceding aspect of the invention, the anti-huCD45 antibody or human CD45-binding antibody fragment, includes:
  (i) an immunoglobulin heavy chain sequence including SEQ ID NO:6 (from mCD45-HC parental), SEQ ID NO:11 (from huCD45.HC1), SEQ ID NO:16 (from huCD45.HC2), SEQ ID NO:21 (from huCD45.HC3), or SEQ ID NO:26 (from huCD45.HC4); and
  (ii) an immunoglobulin light chain sequence including SEQ ID NO:32 (from mCD45-LC parental), SEQ ID NO:37 (from huCD45.LC1), SEQ ID NO:42 (from huCD45.LC2), SEQ ID NO:47 (from huCD45.LC3), or SEQ ID NO:52 (from huCD45.LC4).

Another aspect of the invention provides an anti-huCD45 antibody or a huCD45-binding antibody fragment, including:
  (a) a set of immunoglobulin heavy chain complementarity determining regions (CDRs) including heavy chain CDR1, CDR2 and CDR3 amino acid sequences selected from the following sets:
    (i) SEQ ID NO:53, SEQ ID NO:56, and SEQ ID NO:55, respectively,
    (ii) SEQ ID NO:53, SEQ ID NO:57, and SEQ ID NO:55, respectively, (iii) SEQ ID NO:53, SEQ ID NO:58, and SEQ ID NO:55, respectively, and
(iv) SEQ ID NO:53, SEQ ID NO:54, and SEQ ID NO:55, respectively; and (b) a set of immunoglobulin light chain complementarity determining regions (CDRs) including light chain CDR1, CDR2 and CDR3 amino acid sequences selected from the following sets:
(i) SEQ ID NO:62, SEQ ID NO:60, and SEQ ID NO:61, respectively,
(ii) SEQ ID NO:59, SEQ ID NO:63, and SEQ ID NO:61, respectively,
(iii) SEQ ID NO:59, SEQ ID NO:64, and SEQ ID NO:61, respectively, and.
(iv) SEQ ID NO:59, SEQ ID NO:60, and SEQ ID NO:61, provided that when the heavy chain CDR set is (a)(iv), the light chain CDR set is not (b)(iv).

A related aspect of the invention provides an anti-huCD45 antibody or a huCD45-binding antibody fragment, including:

(a) a set of immunoglobulin heavy chain complementarity determining regions (CDRs) including heavy chain CDR1, CDR2 and CDR3 amino acid sequences selected from the following sets:
(i) SEQ ID NO:53, SEQ ID NO:56, and SEQ ID NO:55, respectively,
(ii) SEQ ID NO:53, SEQ ID NO:57, and SEQ ID NO:55, respectively, and
(iii) SEQ ID NO:53, SEQ ID NO:58, and SEQ ID NO:55, respectively; and (b) a set of immunoglobulin light chain complementarity determining regions (CDRs) including light chain CDR1, CDR2 and CDR3 amino acid sequences selected from the following sets:
(i) SEQ ID NO:62, SEQ ID NO:60, and SEQ ID NO:61, respectively,
(ii) SEQ ID NO:59, SEQ ID NO:63, and SEQ ID NO:61, respectively, and
(iii) SEQ ID NO:59, SEQ ID NO:64, and SEQ ID NO:61, respectively.

Additional features, advantages, and aspects of the invention may be set forth or apparent from consideration of the following detailed description, drawings, and claims. Moreover, it is to be understood that both the foregoing summary of the invention and the following detailed description are exemplary and intended to provide further explanation without limiting the scope of the invention as claimed.

BRIEF DESCRIPTION OF THE DRAWINGS

Various antibody heavy and light chain amino acid sequences are set forth in FIGS. 1-10.

FIG. 1 shows the amino acid sequence of a heavy chain of mouse anti-huCD45 antibody ("m CD45-HC parental") that binds all isoforms of human CD45 (huCD45) and portions thereof used as the basis for producing humanized anti-huCD45 antibodies.

FIG. 2 shows the amino acid sequence of a humanized anti-huCD45 antibody heavy chain ("hu CD45.HC1") and portions thereof.

FIG. 3 shows the amino acid sequence of a humanized anti-huCD45 antibody heavy chain ("hu CD45.HC2") and portions thereof.

FIG. 4 shows the amino acid sequence of a humanized anti-huCD45 antibody heavy chain ("hu CD45.HC3") and portions thereof.

FIG. 5 shows the amino acid sequence of a humanized anti-huCD45 antibody heavy chain ("hu CD45.HC4") and portions thereof.

FIG. 6 shows the amino acid sequence of a light chain of mouse anti-huCD45 antibody ("m CD45-LC parental") and portions thereof used as the basis for producing humanized anti-huCD45 antibodies.

FIG. 7 shows the amino acid sequence of a humanized anti-huCD45 antibody light chain ("hu CD45.LC1") and portions thereof.

FIG. 8 shows the amino acid sequence of a humanized anti-huCD45 antibody light chain ("hu CD45.LC2") and portions thereof.

FIG. 9 shows the amino acid sequence of a humanized anti-huCD45 antibody light chain ("hu CD45.LC3") and portions thereof.

FIG. 10 shows the amino acid sequence of a humanized anti-huCD45 antibody light chain ("hu CD45.LC4") and portions thereof.

Figure 11:
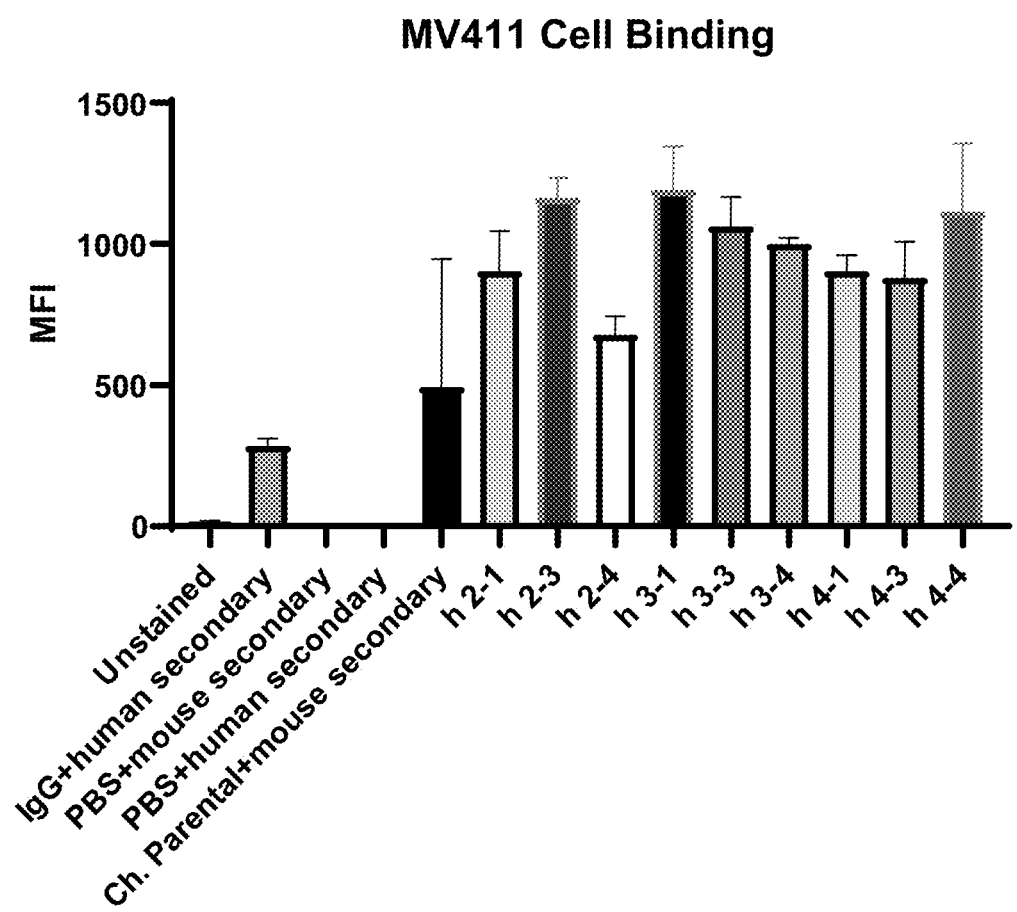
FIG. 11 shows cell binding data for binding of various humanized anti-huCD45 antibodies disclosed herein to MV411 human AML cell line cells, versus controls.

The complementarity determining region (CDR) amino acid sequences are underlined in the presentation of the variable region sequences in the figures.

DETAILED DESCRIPTION

One aspect of the invention provides an anti-(human CD45) ["anti-huCD45"] antibody, comprising:
(i) a heavy chain which is mCD45-HC parental, huCD45.HC1, huCD45.HC2, huCD45.HC3, huCD45.HC1, or huCD45.HC4, or any of said heavy chains without the signal sequence, or a heavy chain comprising the heavy chain variable region of any of said heavy chains; and
(ii) a light chain which is mCD45-LC parental, huCD45.LC1, huCD45.LC2, huCD45.LC3, or huCD45.LC4, or any of said light chains without the signal sequence, or a light chain comprising the light chain variable region of any of said light chains, provided that when the heavy chain is mCD45-HC parental with or without the signal sequence, the light chain is not mCD45-LC parental with or without the signal sequence, or a human CD45-binding fragment of the antibody, such as a Fab fragment or Fab$_2$ fragment or a corresponding scFv molecule.

The parental murine monoclonal antibody including the parental heavy chain shown in FIG. 1 and the parental light chain shown in FIG. 6, which binds all isoforms of human CD45, was used as the basis for designing humanized anti-huCD45 antibodies. Antibodies consisting of various combinations of the humanized immunoglobulin heavy chains and immunoglobulin light chains were expressed in CHO cells and isolated for analysis and comparison to the parental antibody. Binding experiments were performed using an Octet HTX (Sartorius, Bohemia, New York, USA) at 25° C. to determine the KD's of the antibodies. The antibodies were loaded onto anti-human Fc capture (AHC) sensors. The loaded sensors were dipped into serial dilutions of rhCD45 His tag (900 nM start, 1:3 dilution, 3 points; R&D Systems, Minneapolis, MN, USA). Reference sample well (buffer) was used for data analysis. Kinetic constants were calculated using a monovalent (1:1) binding model. Results are shown in Table 1 below.

TABLE 1

| Sample ID | KD (M) |
|---|---|
| m CD45 Parental | 3.75E-08 |
| hu CD45 HC2 + LC1 | 2.44E-07 |
| hu CD45 HC2 + LC3 | 1.96E-07 |
| hu CD45 HC2 + LC4 | 2.47E-07 |
| hu CD45 HC3 + LC1 | 1.63E-07 |
| hu CD45 HC3 + LC3 | 5.02E-08 |
| hu CD45 HC3 + LC4 | 1.09E-07 |
| hu CD45 HC4 + LC1 | 2.32E-07 |
| hu CD45 HC4 + LC3 | 1.51E-07 |
| hu CD45 HC4 + LC4 | 1.23E-07 | hu CD45 HC3+LC3 retained similar binding affinity as the parental antibody while all other humanized samples showed less than 10-fold changes in KD values relative to the parental antibody.

Another aspect of the invention provides an anti-huCD45 antibody or a human CD45-binding antibody fragment, including:
 (i) an immunoglobulin heavy chain variable region including SEQ ID NO:2 (from mCD45-HC parental), SEQ ID NO:7 (from huCD45.HC1), SEQ ID NO:12 (from huCD45.HC2), SEQ ID NO:17 (from huCD45.HC3), or SEQ ID NO:22 (from huCD45.HC4); and
 (ii) an immunoglobulin light chain variable region including SEQ ID NO:28 (from mCD45-LC parental), SEQ ID NO:33 (from huCD45.LC1), SEQ ID NO:38 (from huCD45.LC2), SEQ ID NO:43 (from huCD45.LC3), or SEQ ID NO:48 (from huCD45.LC4),
provided that when the heavy chain variable region includes SEQ ID NO:2, the light chain variable region is not SEQ ID NO:28.

In a variation of the preceding aspect of the invention, the anti-huCD45 antibody or human CD45-binding antibody fragment, includes:
 (i) an immunoglobulin heavy chain sequence including SEQ ID NO:6 (from mCD45-HC parental), SEQ ID NO:11 (from huCD45.HC1), SEQ ID NO:16 (from huCD45.HC2), SEQ ID NO:21 (from huCD45.HC3), or SEQ ID NO:26 (from huCD45.HC4); and
 (ii) an immunoglobulin light chain sequence including SEQ ID NO:32 (from mCD45-LC parental), SEQ ID NO:37 (from huCD45.LC1), SEQ ID NO:42 (from huCD45.LC2), SEQ ID NO:47 (from huCD45.LC3), or SEQ ID NO:52 (from huCD45.LC4).

A further aspect of the invention provides an anti-huCD45 antibody or a huCD45-binding antibody fragment, including:
 (a) a set of immunoglobulin heavy chain complementarity determining regions (CDRs) including heavy chain CDR1, CDR2 and CDR3 amino acid sequences selected from the following sets:
  (i) SEQ ID NO:53, SEQ ID NO:56, and SEQ ID NO:55, respectively,
  (ii) SEQ ID NO:53, SEQ ID NO:57, and SEQ ID NO:55, respectively,
  (iii) SEQ ID NO:53, SEQ ID NO:58, and SEQ ID NO:55, respectively, and
  (iv) SEQ ID NO:53, SEQ ID NO:54, and SEQ ID NO:55, respectively; and
 (b) a set of immunoglobulin light chain complementarity determining regions (CDRs) including light chain CDR1, CDR2 and CDR3 amino acid sequences selected from the following sets:
  (i) SEQ ID NO:62, SEQ ID NO:60, and SEQ ID NO:61, respectively,
  (ii) SEQ ID NO:59, SEQ ID NO:63, and SEQ ID NO:61, respectively,
  (iii) SEQ ID NO:59, SEQ ID NO:64, and SEQ ID NO:61, respectively, and.
  (iv) SEQ ID NO:59, SEQ ID NO:60, and SEQ ID NO:61,
provided that when the heavy chain CDR set is (a)(iv), the light chain CDR set is not (b)(iv). It should be understood that the antibody or antibody fragment includes a heavy chain variable region that includes the heavy chain CDRs and a light chain variable region that includes the light chain CDRs.

A related aspect of the invention provides an anti-huCD45 antibody or a huCD45-binding antibody fragment, including:
 (a) a set of immunoglobulin heavy chain complementarity determining regions (CDRs) including heavy chain CDR1, CDR2 and CDR3 amino acid sequences selected from the following sets:
  (i) SEQ ID NO:53, SEQ ID NO:56, and SEQ ID NO:55, respectively,
  (ii) SEQ ID NO:53, SEQ ID NO:57, and SEQ ID NO:55, respectively, and
  (iii) SEQ ID NO:53, SEQ ID NO:58, and SEQ ID NO:55, respectively; and
 (b) a set of immunoglobulin light chain complementarity determining regions (CDRs) including light chain CDR1, CDR2 and CDR3 amino acid sequences selected from the following sets:
  (i) SEQ ID NO:62, SEQ ID NO:60, and SEQ ID NO:61, respectively,
  (ii) SEQ ID NO:59, SEQ ID NO:63, and SEQ ID NO:61, respectively, and
  (iii) SEQ ID NO:59, SEQ ID NO:64, and SEQ ID NO:61, respectively.

It should again be understood that the antibody or antibody fragment includes a heavy chain variable region that includes the heavy chain CDRs and a light chain variable region that includes the light chain CDRs.

In a variation of either of the preceding two aspects of the invention or of other aspects of the invention in which CDR sequences are recited, the antibody or antibody fragment or protein further includes with respect to one or more of the recited CDRs, in any and all combinations, additional N-terminal and/or C-terminal amino acid sequence, of 1, 2, 3, 4, 5, 6, 7, 8, 9, or 10 amino acid residues immediately adjacent to the one or more CDRs (on either or both of the N-terminal and C-terminal side of the CDR(s)) as shown in the any of the respective variable region amino acid sequences set forth in FIGS. 1-10.

Another aspect of the invention provides a protein, such as an anti-CD45 antibody or CD45-binding antibody fragment (such as Fab fragment, Fab$_2$ fragment, or scFv molecule) or an immunoglobulin light chain, including an antibody light chain variable region including the following light chain CDRs:
- a CDR-L1 including the amino acid sequence RASKSVSTSGYSYLH (SEQ ID NO:59), KSSKSVSTSGYSYLH (SEQ ID NO:62), RASKSVSTSGYSYLA (SEQ ID NO:65), RASKSVSTSGYSYLS (SEQ ID NO:66), or RASKSVSTSGYSYLN (SEQ ID NO:67);
- a CDR-L2 including the amino acid sequence LASNLES (SEQ ID NO: 60), LASNLA (SEQ ID NO:68), LASNLAT (SEQ ID NO:63), LASNLQ (SEQ ID NO:69), LASNLQS (SEQ ID NO:64), LASTRES (SEQ ID NO:70), LASTRAT (SEQ ID NO:71), LASNRAT (SEQ ID NO:72), or LASSQLS (SEQ ID NO:73);
- a CDR-L3 including the amino acid sequence QHSRELPFT (SEQ ID NO:61), provided that the combination of a CDR-L1 including the amino acid sequence RASKSVSTSGYSYLH (SEQ ID NO:59) and CDR-L2 including the amino acid sequence LASNLES (SEQ ID NO:60) is excluded.

The next amino acid residues following the CDR-L3 sequence QHSRELPFT (SEQ ID NO:61) in the protein may, for example, be FGQ.

A further aspect of the invention provides a protein, such as an anti-CD45 antibody or CD45-binding antibody fragment (such as Fab fragment, Fab₂ fragment, or scFv molecule) or an immunoglobulin heavy chain, including an antibody heavy chain variable region including the following light chain CDRs:
- a CDR-H1 including the amino acid sequence GFDFSRYWMS (SEQ ID NO:53) or GFDFSRYWMN (SEQ ID NO:85);
- a CDR-H2 including the amino acid sequence EINPTSSTINFTPSLKD (SEQ ID NO:54), EINPTSSTINFADSVKG (SEQ ID NO:56), EINPTSSTINYADSVKG (SEQ ID NO:57), EINPTSSTINFVDSVKG (SEQ ID NO:58), YINPTSSTIYYADSVKG (SEQ ID NO:74), AINPTSSTIYYADSVKG (SEQ ID NO:75), NINPTSSTIYYVDSVKG (SEQ ID NO:76), or SINPTSSTIYYADSVKG (SEQ ID NO:77);
- a CDR-H3 including the amino acid sequence GNYYRYGDAMDY (SEQ ID NO:55), provided that the combination of a CDR-H1 including the amino acid sequence GFDFSRYWMS (SEQ ID NO:53) and CDR-H2 including the amino acid sequence EINPTSSTINFTPSLKD (SEQ ID NO:54) is excluded.

Still another aspect of the invention provides a protein, such as an anti-CD45 antibody or CD45-binding antibody fragment (such as Fab fragment, Fab₂ fragment, or scFv molecule), including:
(a) an antibody light chain variable region including the following light chain CDRs:
- a CDR-L1 including the amino acid sequence RASKSVSTSGYSYLH (SEQ ID NO:59), KSSKSVSTSGYSYLH (SEQ ID NO:62), RASKSVSTSGYSYLA (SEQ ID NO:65), RASKSVSTSGYSYLS (SEQ ID NO:66), or RASKSVSTSGYSYLN (SEQ ID NO:67);
- a CDR-L2 including the amino acid sequence LASNLES (SEQ ID NO:60), LASNLA (SEQ ID NO:68), LASNLAT (SEQ ID NO:63), LASNLQ (SEQ ID NO:69), LASNLQS (SEQ ID NO:64), LASTRES (SEQ ID NO:70), LASTRAT (SEQ ID NO:71), LASNRAT (SEQ ID NO:72), or LASSQLS (SEQ ID NO:73); and
- a CDR-L3 including the amino acid sequence QHSRELPFT (SEQ ID NO:61); and (b) an antibody heavy chain variable region including the following heavy chain CDRs:
- a CDR-H1 including the amino acid sequence GFDFSRYWMS (SEQ ID NO:53) or GFDFSRYWMN (SEQ ID NO:85);
- a CDR-H2 including the amino acid sequence EINPTSSTINFTPSLKD (SEQ ID NO:54), EINPTSSTINFADSVKG (SEQ ID NO:56), EINPTSSTINYADSVKG (SEQ ID NO:57), EINPTSSTINFVDSVKG (SEQ ID NO:58), YINPTSSTIYYADSVKG (SEQ ID NO:74), AINPTSSTIYYADSVKG (SEQ ID NO:75), NINPTSSTIYYVDSVKG (SEQ ID NO:76), or SINPTSSTIYYADSVKG (SEQ ID NO:77); and
- a CDR-H3 including the amino acid sequence GNYYRYGDAMDY (SEQ ID NO:55), provided that the combination of CDR-L1 including the amino acid sequence RASKSVSTSGYSYLH (SEQ ID NO:59), CDR-L2 including the amino acid sequence LASNLES (SEQ ID NO:60), CDR-L3 including the amino acid sequence QHSRELPFT (SEQ ID NO:61), CDR-H1 including the amino acid sequence GFDFSRYWMS (SEQ ID NO:53), CDR-H2 including the amino acid sequence EINPTSSTINFTPSLKD (SEQ ID NO:54), and CDR-H3 including the amino acid sequence GNYYRYGDAMDY (SEQ ID NO:55) is excluded. The next amino acid residues following the CDR-L3 sequence QHSRELPFT (SEQ ID NO:61) in the protein may, for example, be FGQ.

A further aspect of the invention provides a protein, such as an anti-CD45 antibody or CD45-binding antibody fragment (such as Fab fragment, Fab₂ fragment, or scFv molecule) or an immunoglobulin light chain, including an antibody light chain variable region including the following light chain CDRs:
- a CDR-L1 including the amino acid sequence RASKSVSTSGYSYLH (SEQ ID NO:59) or KSSKSVSTSGYSYLH (SEQ ID NO:62);
- a CDR-L2 including the amino acid sequence LASNLA (SEQ ID NO:68), LASNLAT (SEQ ID NO:63), LASNLQ (SEQ ID NO:69), or LASNLQS (SEQ ID NO:64); and
- a CDR-L3 including the amino acid sequence QHSRELPFT (SEQ ID NO:61).

The next amino acid residues following the CDR-L3 sequence QHSRELPFT (SEQ ID NO:61) in the protein may, for example, be FGQ.

Another aspect of the invention provides a protein, such as an anti-CD45 antibody or CD45-binding antibody fragment (such as Fab fragment, Fab₂ fragment, or scFv molecule) or an immunoglobulin heavy chain, including an antibody heavy chain variable region including the following heavy chain CDRs:
- a CDR-H1 including the amino acid sequence GFDFSRYWMS (SEQ ID NO:53);
- a CDR-H2 including the amino acid sequence EINPTSSTINFADSVKG (SEQ ID NO:56), EINPTSSTINYADSVKG (SEQ ID NO:57), or EINPTSSTINFVDSVKG (SEQ ID NO: 58); and
- a CDR-H3 including the amino acid sequence GNYYRYGDAMDY (SEQ ID NO:55).

A still further aspect of the invention provides a protein, such as an anti-CD45 antibody or CD45-binding antibody fragment (such as Fab fragment, Fab₂ fragment, or scFv molecule), including:

(a) an antibody light chain variable region including the following light chain CDRs:
   a CDR-L1 including the amino acid sequence RASKSVSTSGYSYLH (SEQ ID NO:59) or KSSKSVSTSGYSYLH (SEQ ID NO:62);
   a CDR-L2 including the amino acid sequence LASNLES (SEQ ID NO:60), LASNLA (SEQ ID NO:68), LASNLAT (SEQ ID NO:63), LASNLQ (SEQ ID NO:69), LASNLQS (SEQ ID NO:64); and
   a CDR-L3 including the amino acid sequence QHSRELPFT (SEQ ID NO:61); and
(b) an antibody heavy chain variable region including the following heavy chain CDRs:
   a CDR-H1 including the amino acid sequence GFDFSRYWMS (SEQ ID NO:53);
   a CDR-H2 including the amino acid sequence EINPTSSTINFTPSLKD (SEQ ID NO:54), EINPTSSTINFADSVKG (SEQ ID NO:56), EINPTSSTINYADSVKG (SEQ ID NO:57), or EINPTSSTINFVDSVKG (SEQ ID NO:58); and
   a CDR-H3 including the amino acid sequence GNYYRYGDAMDY (SEQ ID NO:55),
provided that the combination of CDR-L1 including the amino acid sequence RASKSVSTSGYSYLH (SEQ ID NO:59), CDR-L2 including the amino acid sequence LASNLES (SEQ ID NO:60), CDR-L3 including the amino acid sequence QHSRELPFT (SEQ ID NO:61), CDR-H1 including the amino acid sequence GFDFSRYWMS (SEQ ID NO:53), CDR-H2 including the amino acid sequence EINPTSSTINFTPSLKD (SEQ ID NO:54), and CDR-H3 including the amino acid sequence GNYYRYGDAMDY (SEQ ID NO:55) is excluded. The next amino acid residues following the CDR-L3 sequence QHSRELPFT (SEQ ID NO:61) in the protein may, for example, be FGQ. The CDR-H2 may, for example, include the amino acid sequence EINPTSSTINFADSVKG (SEQ ID NO:56), EINPTSSTINYADSVKG (SEQ ID NO:57), or EINPTSSTINFVDSVKG (SEQ ID NO:58).

One aspect of the invention provides an immunoglobulin heavy chain variable region or a protein, such as an anti-CD45 antibody or CD45 binding antibody fragment such as a Fab, $Fab_2$ or scFv molecule, including an immunoglobulin heavy chain variable region sequence that includes one or more of the amino acid substitutions disclosed in any of the non-parental immunoglobulin heavy chain variable regions disclosed herein versus the parental immunoglobulin heavy chain variable region disclosed herein, in any combination, but otherwise includes the same amino acid sequence as the parental immunoglobulin heavy chain variable region sequence.

One aspect of the invention provides an immunoglobulin light chain variable region or a protein, such as an anti-CD45 antibody or CD45 binding antibody fragment such as a Fab, $Fab_2$ or scFv molecule, including an immunoglobulin light chain variable region that includes one or more of the amino acid substitutions disclosed in any of the non-parental immunoglobulin light chain variable regions disclosed herein versus the parental immunoglobulin light chain variable region sequence.

One aspect of the invention provides a protein, such as an anti-CD45 antibody or CD45 binding antibody fragment such as a Fab, $Fab_2$ or scFv molecule, including:
(i) an immunoglobulin heavy chain variable region that includes one or more of the amino acid substitutions disclosed in any of the non-parental immunoglobulin heavy chain variable regions disclosed herein versus the parental immunoglobulin heavy chain variable region disclosed herein, in any combination, but otherwise includes the same amino acid sequence as the parental immunoglobulin heavy chain variable region sequence; and
(ii) an immunoglobulin light chain variable region that includes one or more of the amino acid substitutions disclosed in any of the non-parental immunoglobulin light chain variable regions disclosed herein versus the parental immunoglobulin light chain variable region disclosed herein, in any combination, but otherwise includes the same amino acid sequence as the parental immunoglobulin light chain variable region sequence.

One aspect of the invention provides a protein, such as an anti-CD45 antibody or CD45 binding antibody fragment such as a Fab, $Fab_2$ or scFv molecule, including:
(i) the parental immunoglobulin heavy chain variable region disclosed herein, or
   an immunoglobulin heavy chain variable region that includes one or more of the amino acid substitutions disclosed in any of the non-parental immunoglobulin heavy chain variable regions disclosed herein versus the parental immunoglobulin heavy chain variable region disclosed herein, in any combination, but otherwise includes the same amino acid sequence as the parental immunoglobulin heavy chain variable region sequence; and
(ii) the parental immunoglobulin light chain variable region disclosed herein, or
   an immunoglobulin light chain variable region that includes one or more of the amino acid substitutions disclosed in any of the non-parental immunoglobulin light chain variable regions disclosed herein versus the parental immunoglobulin light chain variable region disclosed herein, in any combination, but otherwise includes the same amino acid sequence as the parental immunoglobulin heavy chain variable region sequence.
provided that the protein does not include both the parental immunoglobulin heavy chain variable region disclosed herein and the parental immunoglobulin light chain variable region disclosed herein.

In one variation of this aspect, the protein does not include the parental immunoglobulin heavy chain variable region disclosed herein and does not include the parental immunoglobulin light chain variable region disclosed herein.

One aspect of the invention provides an immunoglobulin heavy chain variable region or a protein, such as an anti-CD45 antibody or CD45 binding antibody fragment such as a Fab, $Fab_2$ or scFv molecule, including an immunoglobulin heavy chain variable region sequence that includes the amino acid sequence:

(SEQ ID NO: 78)
EVKLLESGGGLVQPGGSLKLSCAASGFDFSRYWMX$_1$WVRQAPGKGLEWX$_2$

X$_3$X$_4$INPTSSTIX$_5$X$_6$X$_7$X$_8$SLKX$_9$X$_{10}$X$_{11}$X$_{12}$ISRDNX$_{13}$KNX$_{14}$LYL

QMSX$_{15}$X$_{16}$RX$_{17}$EDTAX$_{18}$YYCARGNYYRYGDAMDYWGQGTX$_{19}$VTVSS, wherein
X$_1$ is S or N,
X$_2$ is I or V,
X$_3$ is G, S or A,
X$_4$ is E, Y, A, N, or S,
X$_5$ is N or Y, $X_6$ is F or Y,
$X_7$ is T, A, or V,
$X_8$ is P or D,
$X_9$ is D or G,
$X_{10}$ is K or R,
$X_{11}$ is V or F,
$X_{12}$ is F or T,
$X_{13}$ is A or S,
$X_{14}$ is T or S,
$X_{15}$ is K or S,
$X_{16}$ is V or L,
$X_{17}$ is S or A
$X_{18}$ is L or V, and
$X_{19}$ is S or M,
provided that the amino acid sequence does not include the sequence (SEQ ID NO: 2)
EVKLLESGGGLVQPGGSLKLSCAASGFDFSRYWMSWVRQAPGKGLEWIGE

INPTSSTINFTPSLKDKVFISRDNAKNTLYLQMSKVRSEDTALYYCARGN

YYRYGDAMDYWGQGTSVTVSS.

The heavy chain variable region amino acid sequence of this aspect may be referred to herein as "the Modified Heavy Chain Variable Region Sequence" or the "M.H.C.V.R. Sequence".

One aspect of the invention provides an immunoglobulin light chain variable region or a protein, such as an anti-CD45 antibody or CD45 binding antibody fragment such as a Fab, Fab$_2$ or scFv molecule, including an immunoglobulin light chain variable region sequence that includes the amino acid sequence:

(SEQ ID NO: 79)
DIX$_{L1}$X$_{L2}$TQSPX$_{L3}$X$_{L4}$LX$_{L5}$X$_{L6}$SX$_{L7}$GX$_{L8}$RX$_{L9}$TX$_{L10}$X$_{L11}$C

X$_{L32}$X$_{L13}$SKSVSTSGYSYLX$_{L14}$WYQQKPGQX$_{L15}$PX$_{L16}$LLIYLA

SX$_{L17}$X$_{L18}$X$_{L19}$X$_{L20}$GX$_{L21}$PX$_{L22}$RFSGSGSGTDFTLX$_{L23}$I

X$_{L24}$X$_{L25}$X$_{L26}$X$_{L27}$X$_{L28}$EDX$_{L29}$AX$_{L30}$YYCQHSRELPFTFG

X$_{L31}$GTKLEIK, wherein
$X_{L1}$ is D or E,
$X_{L}2$ is A or V or Q,
$X_{L3}$ is L or M,
$X_{L4}$ is A or D or S,
$X_{L5}$ is S or T,
$X_{L6}$ is A or S,
$X_{L7}$ is V or L or A,
$X_{L8}$ is L or P or V,
$X_{L9}$ is Q or E or D,
$X_{L10}$ is A or V,
$X_{L11}$ is I or L,
$X_{L12}$ is S or N or T,
$X_{L13}$ is A or S,
$X_{L14}$ is H, A, S, or N,
$X_{L15}$ is P or A,
$X_{L16}$ is K or R,
$X_{L17}$ is N or T or S,
$X_{L18}$ is L or R,
$X_{L19}$ is E or A or Q,
$X_{L20}$ is S or T,
$X_{L21}$ is V or I,
$X_{L22}$ is A or D or S,
$X_{L23}$ is N or T,
$X_{L24}$ is H or S,
$X_{L25}$ is P or S,
$X_{L26}$ is V or L,
$X_{L27}$ is E or Q,
$X_{L28}$ is E or A or P,
$X_{L29}$ is A or V or F,
$X_{L30}$ is T or V,
$X_{L31}$ is S or Q, and
$X_{L32}$ is R or K.

provided that the amino acid sequence does not include the sequence (SEQ ID NO: 28)
DIALTQSPASLAVSLGQRATISCRASKSVSTSGYSYLHWYQQKPGQPPKL

LIYLASNLESGVPARFSGSGSGTDFTLNIHPVEEEDAATYYCQHSRELPF

TFGSGTKLEIK.

The light chain variable region amino acid sequence of this aspect may be referred to herein as "the Modified Light Chain Variable Region Sequence" or the "M.L.C.V.R. Sequence".

One aspect of the invention provides a protein, such as an anti-CD45 antibody or CD45 binding antibody fragment such as a Fab, Fab$_2$ or scFv molecule, including:
(i) a heavy chain variable region including the M.H.C.V.R. Sequence or the parental heavy chain variable region amino sequence disclosed herein; and
(ii) a light chain variable region including the M.L.C.V.R. Sequence or the parental light chain variable region amino sequence disclosed herein,
provided that the protein does not include both the parental heavy chain variable region amino sequence disclosed herein and the parental light chain variable region amino sequence disclosed herein.

One aspect of the invention provides a protein, such as an anti-CD45 antibody or CD45 binding antibody fragment such as a Fab, Fab$_2$ or scFv molecule, including:
(i) a heavy chain variable region including the M.H.C.V.R. Sequence; and
(ii) a light chain variable region including the M.L.C.V.R. Sequence.

One aspect of the invention provides a protein, such as a CD45 binding scFv molecule or a protein including at least one scFv segment, that includes a consecutive (amino to carboxy terminal order) amino acid sequence that includes amino acids 1-120 (the amino acids through and including the sequence VTVS or corresponding amino acid positions) or amino acids 1-121 of a heavy chain variable region as disclosed herein, followed by a linker amino acid sequence, followed by the amino acid sequence of a light chain variable region disclosed herein, provided that the protein does not include both amino acids 1-120 of the parental heavy chain variable region sequence disclosed herein and the parental light chain variable region sequence disclosed herein. In one variation, the protein does not include either of amino acids 1-120 of the parental heavy chain variable region sequence disclosed herein and the parental light chain variable region sequence disclosed herein.

The linker amino acid sequence may, for example, include any of the amino acid sequences:

KISGGGGSGGGGSGGGGSGGGGSGGGGSS (SEQ ID NO:80);

SPNSASHSGSAPQTSSAPGSQ (SEQ ID NO:81);

(G3S)$_n$ where, for example, n is 1, 2, 3, 4, 5, 6, 7, 8, 9, or 10, such as (G3S)$_4$, i.e., GGGSGGGSGGGSGGGS (SEQ ID NO:82); or (G4S)$_n$, i.e., (GGGGS [SEQ ID NO:83])$_n$ where, for example, n is 1, 2, 3, 4, 5, 6, 7, 8, 9, or 10, such as (G4S)$_5$, i.e., GGGGSGGGGSGGGGSGGGGSGGGGS, (SEQ ID NO:84).

The heavy chain variable region and light chain variable regions disclosed herein each include three (3) complementarity determining regions (CDRs). The CDRs are surrounded by immunoglobulin framework regions (FRs) in the following manner: FR1 is the amino acid sequence preceding (N-terminal to) CDR1, FR2 is the amino acid sequence between CDR1 and CDR2, FR3 is the amino acid sequence between CDR2 and CDR3, and FR4 is the amino acid sequence following (C-terminal to) CDR3 to the end of the variable region sequence.

As used herein, the term "antibody fragment" includes without limitation proteolytic fragments of antibodies, such as Fab or Fab$_2$ (F(ab')$_2$) fragments, recombinant antibody fragments with covalently associated or non-covalently associated chains, scFv molecules, and rIgG fragments ("rIgG" refers to reduced IgG (~75,000 daltons)) also known as half-IgG.

The proteins, such as antibodies and antibody fragments, may, for example, be linked directly or indirectly, via a chemically conjugated chelator, to a radionuclide, for example, to target cytotoxic radiation to CD45-expressing cells in mammalian subject such as a human patient, or to non-cytotoxically image CD45-expression in a mammalian subject such as a human patient. For example, the antibody may be directly labeled with $^{131}$I according to the methods disclosed in U.S. Pat. No. 10,420,851 or the antibody may be chemically conjugated to a chelator, such as p-SCN-DOTA and labeled with a radionuclide $^{225}$Ac, according to the procedures described in U.S. Pat. No. 9,603,954.

The radionuclide may, for example, be selected from $^{131}$I, $^{125}$I, $^{123}$I, $^{32}$P, $^{213}$Po, $^{134}$Ce, $^{43}$Sc, $^{44}$Sc, $^{47}$Sc, $^{55}$Co, $^{60}$Cu, $^{61}$Cu, $^{62}$Cu, $^{64}$Cu, $^{67}$Cu, $^{66}$Ga, $^{67}$Ga, $^{68}$Ga, $^{82}$Rb, $^{86}$Y, $^{87}$Y, $^{90}$Y, $^{89}$Zr, $^{97}$Ru, $^{105}$Rh, $^{109}$Pd, $^{111}$In, $^{117m}$Sn, $^{149}$Pm, $^{149}$Tb, $^{161}$Tb, $^{153}$Sm, $^{177}$Lu, $^{186}$Re, $^{188}$Re, $^{199}$Au, $^{201}$Tl, $^{137}$Cs, $^{223}$Ra, $^{203}$Pb, $^{212}$Pb, $^{211}$At, $^{212}$Bi, $^{213}$Bi, $^{225}$Ac, and $^{227}$Th.

The chelator group in the various aspects of the invention may, for example, include: 1,4,7,10-tetraazacyclododecane-1,4,7-triacetic acid (DO3A) or a derivative thereof; 1,4,7-triazacyclononane-1,4-diacetic acid (NODA) or a derivative thereof; 1,4,7-triazacyclononane-1,4,7-triacetic acid (NOTA) or a derivative thereof; 1,4,7,10-tetraazacyclododecane-1,4,7,10-tetraacetic acid (DOTA) or a derivative thereof; 1,4,7-triazacyclononane, 1-glutaric acid-4,7-diacetic acid (NODAGA) or a derivative thereof; 1,4,7,10-tetraazacyclodecane, 1-glutaric acid-4,7,10-triacetic acid (DOTAGA) or a derivative thereof; 1,4,8,11-tetraazacyclotetradecane-1,4,8,11-tetraacetic acid (TETA) or a derivative thereof; 1,4,8,11-tetraazabicyclo[6.6.2]hexadecane-4,11-diacetic acid (CB-TE2A) or a derivative thereof; diethylene triamine pentaacetic acid (DTPA), its diester, or a derivative thereof; 2-cyclohexyl diethylene triamine pentaacetic acid (CHX-A"-DTPA) or a derivative thereof; deforoxamine (DFO) or a derivative thereof; 1,2-[[6-carboxypyridin-2-yl]methylamino]ethane (H$_2$dedpa) or a derivative thereof; DADA or a derivative thereof; 1,4,7,10-Tetraazacyclododecane-1,4,7,10-tetra(methylene phosphonic acid) (DOTP) or a derivative thereof; 4-amino-6-[[16-[(6-carboxypyridin-2-yl)methyl]-1,4,10,13-tetraoxa-7,16-diazacyclooctadec-7-yl]methyl]pyridine-2-carboxylic acid (MACROPA-NH$_2$) or a derivative thereof; MACROPA or a derivative thereof; 1,4,7,10-tetrakis(carbamoylmethyl)-1,4,7,10-tetraazacyclododecane (TCMC) or a derivative thereof; {4-[2-(bis-carboxymethylamino)-ethyl]-7-carboxymethyl-[1,4,7]triazonan-1-yl}-acetic acid (NETA) or a derivative thereof; Diamsar or a derivative thereof; 1,4,7-triazacyclononane-1,4,7-tris[methyl(2-carboxyethyl)phosphinic acid (TRAP, PRP9, TRAP-Pr) or a derivative thereof; N,N'-bis(6-carboxy-2-pyridylmethyl)ethylenediamine-N,N'-diacetic acid (H4octapa) or a derivative thereof; N,N'-[1-benzyl-1,2,3-triazole-4-yl]methyl-N,N'-[6-(carboxy)pyridin-2-yl]-1,2-diaminoethane (H2azapa) or a derivative thereof; —N,N"-[[6-(carboxy)pyridin-2-yl]methyl]diethylenetriamine-N,N',N"-triacetic acid (H5decapa) or a derivative thereof; N,N'-bis(2-hydroxy-5-sulfobenzyl)ethylenediamine-N,N'-diacetic acid (SHBED) or a derivative thereof; N,N'-bis(2-hydroxybenzyl)ethylenediamine-N,N'-diacetic acid (HBED) or a derivative thereof; 3,6,9,15-tetraazabicyclo[9.3.1]pentadeca-1(15),11,13-triene-3,6,9-triacetic acid (PCTA) or a derivative thereof; desferrioxamine B (DFO) or a derivative thereof; N,N'-(methylenephosphonate)-N,N'-[6-(methoxycarbonyl)pyridin-2-yl]methyl-1,2-diaminoethane (H6phospa) or a derivative thereof; 1,4,7,10,13,16-hexaazacyclohexadecane-N,N',N",N''',N'''',N'''''-hexaacetic acid (HEHA) or a derivative thereof; 1,4,7,10,13-pentaazacyclopentadecane-N,N',N",N''',N''''-pentaacetic acid (PEPA) or a derivative thereof; or 3,4,3-LI(1,2-HOPO) or a derivative thereof.

The proteins, such as antibodies and antibody fragments, may, for example, be linked to one or more cytotoxic drugs to target and deplete CD45-expressing cells in a mammalian subject such as a human patient. Thus, one aspect of the invention provides an antibody-drug-conjugate (ADC) that includes an antibody or antigen-binding antibody fragment according to the invention as a component. The ADC may, for example, be a conjugate with a cytotoxin containing a benzodiazepine moiety, for example. a pyrrolobenzodiazepine (PBD) or an indolinobenzodiazepine (IGN) moiety, as disclosed in U.S. Pub. No. 20220175951.

The words "comprising" and forms of the word "comprising" as well as the word "including" and forms of the word "including," as used in this description and in the claims, do not limit the inclusion of elements beyond what is referred to. Additionally, although throughout the present disclosure various aspects or elements thereof are described in terms of "including" or "comprising," corresponding aspects or elements thereof described in terms of "consisting essentially of" or "consisting of" are similarly disclosed. For example, while certain aspects of the invention have been described in terms of a protein "including" or "comprising" one or more particular amino acid sequences, corresponding aspects instead reciting a protein "consisting essentially of" or "consisting of" the one or more particular amino acid sequences are also within the scope of said aspects and disclosed by this disclosure.

In addition, compositions including a radiolabeled antibody may include one or more pharmaceutically acceptable carriers or pharmaceutically acceptable excipients. Such carriers are well known to those skilled in the art. For example, injectable drug delivery systems include solutions, suspensions, gels, microspheres and polymeric injectables, and can include excipients such as solubility-altering agents (e.g., ethanol, propylene glycol and sucrose) and polymers (e.g., polycaprolactones and PLGA's). An exemplary formulation may be as substantially described in U.S. Pat. No. 10,420,851 or International Pub. No. WO 2017/155937, incorporated by reference herein. For example, according to certain aspects, the formulation may include 0.5% to 5.0% (w/v) of an excipient selected from the group consisting of ascorbic acid, polyvinylpyrrolidone (PVP), human serum albumin (HSA), a water-soluble salt of HSA, and mixtures thereof. Certain formulations may include 0.5-5% ascorbic acid; 0.5-4% polyvinylpyrrolidone (PVP); and the monoclonal antibody in 50 mM PBS buffer, pH 7.

The humanized and various anti-huCD45 antibodies disclosed herein may, for example, be labeled with a radionuclide, such as $^{131}$I, $^{177}$Lu, $^{211}$At, $^{227}$Th or $^{225}$Ac, or conjugated to a cytotoxic drug, for use as a conditioning agent in preparation of a bone marrow transplant (BMT) or of a hematopoietic stem cell transplant (HSCT), for example, for the treatment of a hematological cancer, or in preparation of administration of a genetically engineered cell therapy such as a CAR-T therapy for the treatment of a cancer, or for use as a direct treatment of a hematological cancer, such as a myeloid or lymphoid hematological cancer. such as a leukemia, for example acute myeloid leukemia (AML), or a lymphoma, for example non-Hodgkin lymphoma (NHL), or for use as an immunological resetting agent in the treatment of an autoimmune disease such as multiple sclerosis, or otherwise in the treatment of an autoimmune disease. The hematological cancer or disorder treated may, for example, be a leukemia (such as acute myeloid leukemia (AML), acute promyelocytic leukemia, acute lymphoblastic leukemia (ALL), acute mixed lineage leukemia, chronic myeloid leukemia (CML), chronic lymphocytic leukemia (CLL), hairy cell leukemia, or large granular lymphocytic leukemia), myelodysplastic syndrome (MDS), a myeloproliferative disorder (such as polycythemia vera, essential thrombocytosis, primary myelofibrosis or chronic myeloid leukemia), multiple myeloma, MGUS and similar disorders, a lymphoma (such as Hodgkin's lymphoma (HL), non-Hodgkin lymphoma (NHL), primary mediastinal large B-cell lymphoma, diffuse large B-cell lymphoma, follicular lymphoma, transformed follicular lymphoma, splenic marginal zone lymphoma, lymphocytic lymphoma, or T-cell lymphoma), or another B-cell malignancy. In one aspect, the radiolabeled or drug-conjugated anti-huCD45 antibody is administered as a maintenance therapy to a subject who previously received a BMT or HSCT in treatment of a hematological cancer such as AML or another described herein, for example, to treat or to prevent a relapse or recurrence of the cancer. Further, the humanized and various anti-huCD45 antibodies disclosed herein may, for example, be labeled with a radionuclide, such as $^{131}$I, $^{177}$Lu, $^{211}$At, $^{227}$Th or $^{225}$Ac, or conjugated to a cytotoxic drug, for use, such as in a non-myeloablative dose, in the prevention or treatment of graft versus host disease (GVHD) or other immunological intolerance to the transplanted organ/tissue and, more generally, to promote immunological tolerance of a transplanted solid organ or solid organ tissue by the host, in a solid organ transplant setting. In one aspect, a non-myeloablative amount of a radiolabeled anti-huCD45 antibody as disclosed herein is administered to a human solid organ transplant patient after the solid organ transplantation, in order to the prevent, reduce, or treat graft versus host disease (GVHD) or other immunological intolerance and, more generally, to promote immunological tolerance of a transplanted solid organ in a host. In each case described here, the subject may be a mammal such as a human patient.

Another aspect of the invention provides use of a radiolabeled anti-huCD45 antibody as disclosed herein in the preparation of a medicament for one or more of (i) myeloablative conditioning in a human patient such as in preparation for a bone marrow transplant or a hematopoietic stem cell transplant, (ii) non-myeloablative conditioning such as for preparation of a human patient to receive cell therapy in the treatment of a hematological malignancy or solid tumor cancer, such as a CAR-T, recombinant TCR T-cell, or CAR-NK cell therapy, or receive cell therapy in the treatment of a non-cancerous (non-malignant) genetic disorder such as β-thalassemia or sickle cell anemia, (iii) direct treatment of a hematological cancer in a human patient such as any of those described above, (iv) use, for example, as an immunological resetting agent, in the treatment of an autoimmune disease such as multiple sclerosis in a human patient, and (v) use in preventing, reducing, or treating graft versus host disease (GVHD) or other immunological intolerance and, more generally, to promote immunological tolerance of a transplanted solid organ in a human patient. The CAR-T cell therapy may, for example, include Kymriah® (tisagenlecleucel; target CD19), Yescarta® (axicabtagene ciloleucel; target CD19), Tecartus® (brexucabtagene autoleucal; target CD19), Breyanzi® (lisocabtagene maraleucel; target CD19), Abecma® (idecabtagene vicleucel; target BCMA), or Carvykti® (ciltacabtagene autoleucel; target BCMA).

Example 1: Production of a Radiolabeled Chelator-Conjugated Anti-huCD45 Antibody Conjugation to a chelator: A vial of lyophilized p-SCN-Bn-DOTA is reconstituted with metal-free water to a concentration of 10 mg/ml. To the actinium reaction vial, 0.02 ml of ascorbic acid solution (150 mg/ml) and 0.05 ml of reconstituted p-SCN-Bn-DOTA are added and the pH adjusted to between 5 and 5.5 with 2M tetramethylammonium acetate (TMAA). The mixture is then heated at 55±4° C. for 30 minutes.

To determine the labeling efficiency of the $^{225}$Ac-p-SCN-Bn-DOTA, an aliquot of the reaction mixture is removed and applied to a 1 ml column of Sephadex C25 cation exchange resin. The product is eluted in 2-4 ml fractions with a 0.9% saline solution. The fraction of $^{225}$Ac activity that elutes is $^{225}$Ac-p-SCN-Bn-DOTA and the fraction that is retained on the column is un-chelated, unreactive $^{225}$Ac. Typically, the labeling efficiency is greater than 95%.

To the reaction mixture, 0.22 ml of previously prepared anti-CD45 mAb in DTPA (1 mg) and 0.02 ml of ascorbic acid are added. The DTPA is added to bind any trace amounts of metals that may compete with the labeling of the antibody. The ascorbic acid is added as a radio-protectant. The pH is adjusted with carbonate buffer to pH 8.5-9. The mixture is heated at 37±3° C. for 30 minutes.

The final product may be purified by size exclusion chromatography using 10DG resin and eluted with 2 ml of 1% HSA.

Radiolabeling: The antibody may be conjugated to a linker, such as any of the linkers described in the above indicated patent applications. An exemplary linker includes at least dodecane tetraacetic acid (DOTA), wherein a goal of the conjugation reaction is to achieve a DOTA-antibody ratio of 3:1 to 5:1. Chelation with the radionuclide, such as $^{177}$Lu, $^{90}$Y, or $^{225}$Ac may then be performed and efficiency and purity of the resulting radiolabeled antibody, such as an anti-CD45 antibody, may be determined by HPLC and iTLC.

An exemplary labeling reaction for $^{225}$Ac is as follows: A reaction including 15 μl 0.15M NH$_4$OAc buffer, pH=6.5 and 2 μL (10 μg) DOTA-anti-CD45 (5 mg/ml) may be mixed in an Eppendorf reaction tube, and 4 μL $^{225}$Ac (10 μCi) in 0.05 M HCl subsequently added. The contents of the tube may be mixed with a pipette tip and the reaction mixture incubated at 37° C. for 90 min with shaking at 100 rpm. At the end of the incubation period, 3 μL of a 1 mM DTPA solution may be added to the reaction mixture and incubated at room temperature for 20 min to bind the unreacted $^{225}$Ac into the $^{225}$Ac-DTPA complex. Instant thin layer chromatography with 10 cm silica gel strip and 10 mM EDTA/normal saline mobile phase may be used to determine the radiochemical purity of $^{225}$Ac-DOTA-anti-CD45 through separating $^{225}$Ac-labeled anti-CD45 ($^{225}$Ac-DOTA-anti-CD45) from free $^{225}$Ac ($^{225}$Ac-DTPA). In this system, the radiolabeled antibody stays at the point of application and $^{225}$Ac-DTPA moves with the solvent front. The strips may be cut in halves and counted in the gamma counter equipped with the multichannel analyzer using channels 72-110 for $^{225}$Ac to exclude its daughters.

Purification: An exemplary radiolabeled targeting agent, such as $^{225}$Ac-DOTA-antibody, may be purified either on PD10 columns pre-blocked with 1% HSA or on Vivaspin centrifugal concentrators with a 50 kDa MW cut-off with 2×1.5 mL washes, 3 min per spin. HPLC analyses of the $^{225}$Ac-DOTA-antibody after purification may be conducted using a Waters HPLC system equipped with flow-through Waters UV and Bioscan Radiation detectors, using a TSK3000SW XL column eluted with PBS at pH=7.4 and a flow rate of 1 ml/min.

Example 2: Radio-Iodination of Anti-huCD45 Antibody and Purification in the Presence of Ascorbic Acid Anti-CD45 antibodies may be radio-iodinated according to the following method.

One mg of an anti-CD45 antibody is labeled with 20 to 30 mCi of $^{131}$I—Na (30 mCi) in the presence of chloramine-T (23 micrograms) in PBS buffer (pH 7.2). The reaction is quenched with the addition of aqueous sodium thiosulfate (69 micrograms) and diluted with cold NaI (1 mg). Immediately following, a concentrated ascorbic acid solution made in 50 mM PBS (pH 7) is added to achieve 2.5% (w/v) ascorbic acid strength in the quenched reaction mixture. Labeling reactions up to 3,000 mCi per batch may, for example, be successfully performed using this method.

The radiolabeled antibody, such as radiolabeled immunoglobulin, can be purified by gel filtration on a sterile, pre-packed commercially available Sephadex G25 column (GE HiPrep 26/10 column, bed volume 53 mL) using PBS (50 mM, pH 7) mobile phase supplemented with 2.5% (w/v) ascorbic acid to stabilize the radiolabeled product. Up to 1,000 mCi reaction volume can be purified on a single column. The product can be collected in a 5 to 35 mL elution volume from the column.

Radio-iodinated reaction batches of <200 mCi may be purified in a similar fashion on a smaller desalting column (GE PD10 column, bed volume 8.6 mL).

Example 3: Radio-Iodination of Anti-CD45 Immunoglobulin and Purification in the Presence of Ascorbic Acid and HSA The radio-iodination and purification may be performed essentially as described in Example 2, except that 2% or 4% (w/v) HSA is also added along with 2.5% (w/v) ascorbic acid to the quenched reaction as well as in the elution buffer during the purification process.

Experiments were further performed to characterize the cell binding attributes of the various humanized anti-huCD45 antibodies disclosed herein against three different human AML cell lines, to compare the cell killing performance of selected $^{225}$Ac-labeled humanized anti-huCD45 antibodies and $^{225}$Ac-labeled parental antibody at different radiation doses, and to evaluate the biodistribution of selected radiolabeled humanized anti-huCD45 antibodies in a murine HL60 xenotransplant tumor model, as described below.

Cell Binding

The cell binding of humanized anti-huCD45 antibody clones was evaluated using flow cytometry. MV411, HL60 or U937 cells were plated at 1×10$^6$ cells per well and incubated with humanized BC8, chimeric parental mAb ("Ch. Parental") or parental mAb (fully murine) at a concentration of 100 μg/mL and incubated for one hour at 4° C. An anti-human secondary ("human secondary") antibody or anti-mouse secondary ("mouse secondary) antibody was added to the cells and incubated for thirty minutes at 4° C. Cell binding mean fluorescence intensity (MFI) was detected by measuring the cell staining signal with a BD Accuri C6 flow cytometer and data analyzed using BD Accuri software. The tested humanized anti-huCD45 mAbs are identified in the figures with "h" followed first by the humanized heavy chain identification number and then the humanized light chain identification number. IgG indicated non-specific immunoglobulin primary antibody control. The chimeric parental anti-huCD45 mAb ("Ch. Parental") having the murine variable regions of the parental antibody and human constant regions was prepared in order to provide more direct comparisons in experiments using anti-human secondary antibody.

FIG. 11 shows cell binding data for binding of various humanized anti-huCD45 antibodies disclosed herein to MV411 human AML cell line cells, versus controls.

Figure 12:
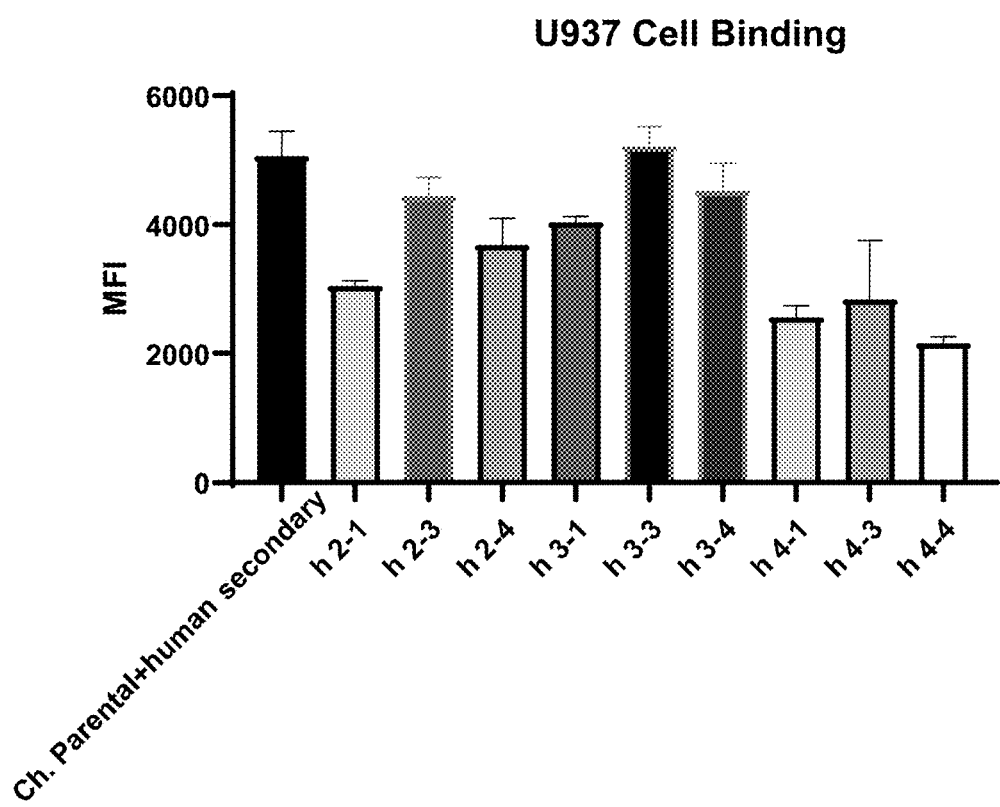
FIG. 12 shows cell binding data for binding of various humanized anti-huCD45 antibodies disclosed herein to U937 human pro-monocytic myeloid leukemia cell line cells, versus controls.

FIG. 12 shows cell binding data for binding of various humanized anti-huCD45 antibodies disclosed herein to U937 human pro-monocytic myeloid leukemia cell line cells, versus controls.

Figure 13:
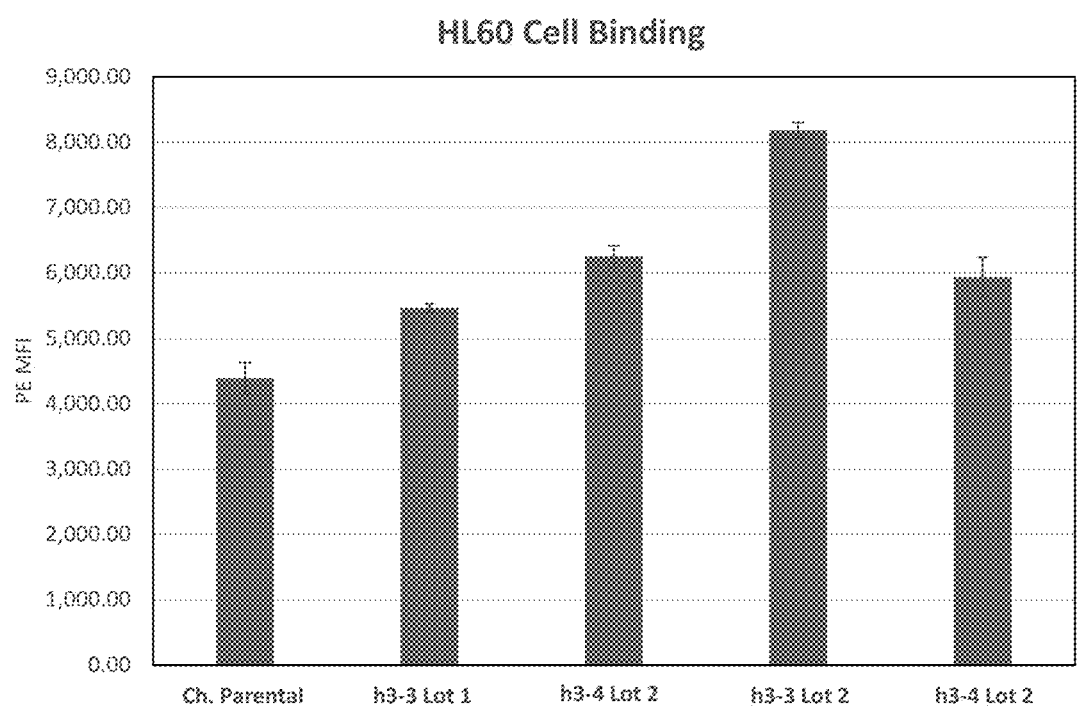
FIG. 13 shows cell binding data for binding of various humanized anti-huCD45 antibodies disclosed herein to HL60 human, promyelocytic AML cell line cells, versus a modified chimeric parental control antibody.

FIG. 13 shows cell binding data for binding of various humanized anti-huCD45 antibodies disclosed herein to HL60 human, promyelocytic AML cell line cells, versus a modified chimeric parental control antibody.

Cell Viability

Figure 14:
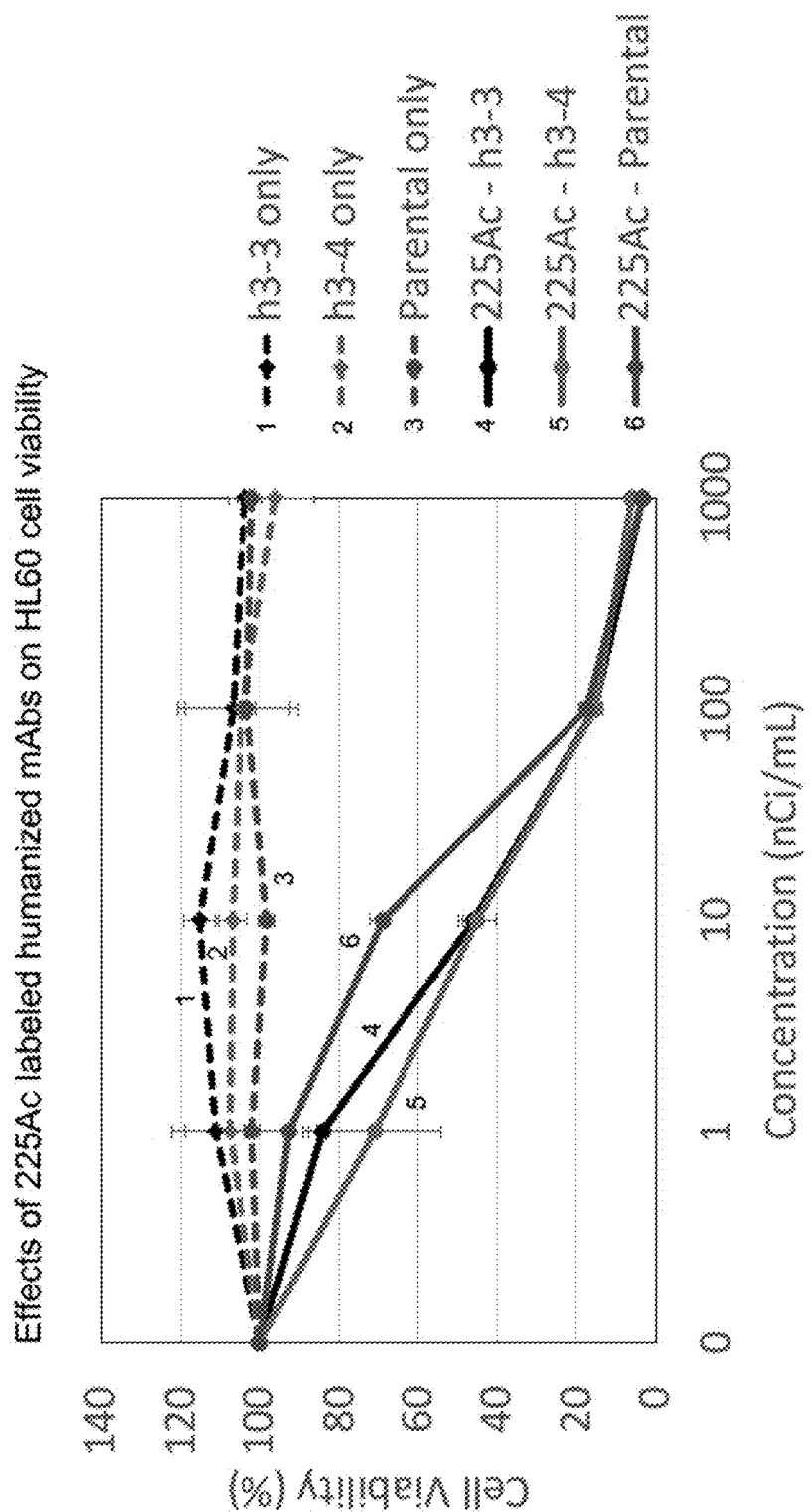
FIG. 14 shows cell viability data for HL60 cells treated with $^{225}$Ac-labeled anti-huCD45 antibodies as disclosed herein, 225Ac-labeled parental antibody, or corresponding unlabeled control antibodies.

To determine cell viability effects, HL60 cells were plated at 1×10$^5$ cells per well and two selected humanized anti-hu CD45 mAbs (h 3-3 and h 3-4, from two different lots each) or parental mAb (fully murine) were added to the cells at a concentration range of 1 to 1,000 nCi/mL (Actinium-225 radiolabeled, 1, 10, 100 and 1,000 nCi/mL tested) and 0.00163 μg/mL to 7.84 μg/mL (non-radiolabeled). After incubating at 37° C. for 72 hours, the cells were washed with PBS and stained with BD Via-Probe Red Nucleic Acid Stain. Cell viability was detected by measuring the cell staining signal with a BD Accuri C6 flow cytometer and data analyzed using GraphPad Prism software. FIG. 14 shows the resulting cell viability data. The non-radiolabeled humanized and parental antibodies had little or no negative effect on cell viability while the corresponding $^{225}$Ac-labeled antibodies increasingly and significantly reduced cell viability with increasing radiation dose.

Biodistribution

BALB/c nude mice bearing human HL60 subcutaneous tumor xenografts were prepared and dosed with Indium-111 radiolabeled humanized anti-huCD45 mAbs (h 3-3 and h 3-4) or parental anti-huCD45 mAb at 50 µCi (2-3 mice per group). After 24, 120 and 168 hours, the blood, tumors, and organ tissues were harvested, weighed and measured for radioactivity. The percentage injected dose per gram tissue (% ID/g) was determined and data analyzed using GraphPad Prism software. The biodistribution data is shown in Table 2 below.

TABLE 2

| | % ID/g | | | | | |
|---|---|---|---|---|---|---|
| | Parental | | HC3 + LC3 | | HC3 + LC4 | |
| Organ | Mean | SD | Mean | SD | Mean | SD |
| Blood | 5.893 | 2.612 | 4.693 | 2.984 | 2.695 | 0.898 |
| Brain | 0.193 | 0.040 | 0.127 | 0.050 | 0.085 | 0.021 |
| Heart | 1.973 | 0.959 | 1.563 | 0.765 | 1.000 | 0.269 |
| Lung | 3.517 | 1.135 | 2.943 | 1.075 | 1.935 | 0.530 |
| Spleen | 7.233 | 0.976 | 7.297 | 3.863 | 6.535 | 0.064 |
| Kidneys | 3.073 | 0.682 | 3.043 | 0.827 | 2.770 | 0.297 |
| Muscle | 0.560 | 0.265 | 0.500 | 0.115 | 0.250 | 0.000 |
| Bone | 1.497 | 0.510 | 1.737 | 0.753 | 2.100 | 1.188 |
| Tumor | 15.083 | 2.527 | 11.580 | 5.240 | 10.180 | 0.764 |
| Stomach | 0.537 | 0.222 | 0.380 | 0.085 | 0.450 | 0.127 |

TABLE 2-continued

| | % ID/g | | | | | |
|---|---|---|---|---|---|---|
| | Parental | | HC3 + LC3 | | HC3 + LC4 | |
| Organ | Mean | SD | Mean | SD | Mean | SD |
| Small Intestine | 0.793 | 0.407 | 0.590 | 0.208 | 0.845 | 0.092 |
| Large Intestine | 0.553 | 0.164 | 0.380 | 0.184 | 0.570 | 0.127 |
| Liver | 8.557 | 0.379 | 5.790 | 2.786 | 8.710 | 0.113 |

These data show that the tested humanized anti-huCD45 antibodies and the parental anti-huCD45 antibody accumulate strongly and comparably in the HL60 tumor and have comparable and expected biodistribution among the organs.

The radiolabeled antibodies used in the preceding experiments were prepared by chemical conjugation of the respective antibodies to the bifunctional chelator p-SCN-Bn-DOTA (S-2-(4-Isothiocyanatobenzyl)-1,4,7,10-tetraazacyclododecane tetraacetic acid; Catalog. No. B-205, Macrocyclics, Inc., Plano, Texas, USA) followed by radiolabeling of the conjugate by chelation of the radionuclide, $^{225}$Ac or $^{111}$In, to the DOTA moiety of the respective conjugate.

While various specific embodiments have been illustrated and described herein, it will be appreciated that various changes can be made without departing from the spirit and scope of the invention(s). Moreover, features described in connection with one aspect of the invention may be used in conjunction with other aspects of the invention, even if not explicitly exemplified in combination within.

What is claimed is:

1. An anti-huCD45 antibody or a huCD45-binding antibody fragment, comprising:
   (i) an immunoglobulin heavy chain variable region comprising SEQ ID NO:17, SEQ ID NO:7, SEQ ID NO:12, SEQ ID NO:22, or SEQ ID NO:2; and
   (ii) an immunoglobulin light chain variable region comprising SEQ ID NO:43, SEQ ID NO:48, SEQ ID NO:33, SEQ ID NO:38, or SEQ ID NO:28,
   provided that when the heavy chain variable region comprises SEQ ID NO:2, the light chain variable region is not SEQ ID NO:28.

2. The anti-huCD45 antibody or huCD45-binding antibody fragment of claim 1, comprising:
   (i) an immunoglobulin heavy chain sequence comprising SEQ ID NO:21, SEQ ID NO:26, SEQ ID NO:11, SEQ ID NO:16, or SEQ ID NO:6; and
   (ii) an immunoglobulin light chain sequence comprising SEQ ID NO:47, SEQ ID NO:52, SEQ ID NO:37, SEQ ID NO:42, or SEQ ID NO:32.

3. An anti-huCD45 antibody or huCD45-binding antibody fragment, comprising:
   (a) a set of immunoglobulin heavy chain complementarity determining regions (CDRs) comprising heavy chain CDR1, CDR2 and CDR3 amino acid sequences selected from the following sets:
      (i) SEQ ID NO:53, SEQ ID NO:58, and SEQ ID NO:55, respectively,
      (ii) SEQ ID NO:53, SEQ ID NO:56, and SEQ ID NO:55, respectively, and
      (iii) SEQ ID NO:53, SEQ ID NO:57, and SEQ ID NO:55, respectively; and
   (b) a set of immunoglobulin light chain complementarity determining regions (CDRs) comprising light chain CDR1, CDR2 and CDR3 amino acid sequences selected from the following sets:
      (i) SEQ ID NO:59, SEQ ID NO:63, and SEQ ID NO:61, respectively, and
      (ii) SEQ ID NO:59, SEQ ID NO:64, and SEQ ID NO:61, respectively, and
      (iii) SEQ ID NO:62, SEQ ID NO:60, and SEQ ID NO:61, respectively.

4. A pharmaceutical composition comprising the antibody or antibody fragment of claim 1 and at least one pharmaceutically acceptable excipient.

5. A radiopharmaceutical composition comprising:
   the antibody or antibody fragment of claim 1;
   a radionuclide linked to the antibody or antibody fragment, and
   at least one pharmaceutically acceptable excipient.

6. The radiopharmaceutical composition of claim 5, wherein the radionuclide is an alpha particle emitter or a beta particle emitter.

7. The radiopharmaceutical composition of claim 5, wherein the radionuclide comprises $^{131}$I.

8. The radiopharmaceutical composition of claim 5, wherein the radionuclide comprises $^{225}$Ac, $^{177}$Lu or $^{90}$Y.

9. A composition comprising the antibody or antibody fragment of claim 1, chemically conjugated to a chelator.

10. The composition of claim 9, wherein the chelator comprises DOTA or a DOTA derivative.

11. The composition of claim 9, further comprising a radionuclide chelated by the chelator.

* * * * *